United States Patent
Harding et al.

(10) Patent No.: US 11,202,914 B2
(45) Date of Patent: Dec. 21, 2021

(54) PASSIVE PROPAGATION FRACTAL ANTENNA FOR INTRABODY TRANSMISSIONS

(71) Applicant: Medtronic, Inc., Minneapolis, MN (US)

(72) Inventors: William C. Harding, Chandler, AZ (US); Martha De Cunha Maluf-Burgman, The Hague (NL)

(73) Assignee: Medtronic, Inc., Minneapolis, MN (US)

( * ) Notice: Subject to any disclaimer, the term of this patent is extended or adjusted under 35 U.S.C. 154(b) by 188 days.

(21) Appl. No.: 16/230,273

(22) Filed: Dec. 21, 2018

(65) Prior Publication Data

US 2020/0197710 A1 Jun. 25, 2020

(51) Int. Cl.
| | |
|---|---|
| *A61N 1/372* | (2006.01) |
| *G16H 20/40* | (2018.01) |
| *G08C 17/02* | (2006.01) |
| *H01Q 1/27* | (2006.01) |
| *H01Q 15/00* | (2006.01) |
| *A61N 1/36* | (2006.01) |
| *A61N 1/05* | (2006.01) |
| *A61N 1/378* | (2006.01) |
| *A61N 1/02* | (2006.01) |
| *H02J 50/20* | (2016.01) |

(52) U.S. Cl.
CPC ......... *A61N 1/37229* (2013.01); *A61N 1/025* (2013.01); *A61N 1/0534* (2013.01); *A61N 1/36125* (2013.01); *A61N 1/36128* (2013.01); *A61N 1/3787* (2013.01); *G08C 17/02* (2013.01); *G16H 20/40* (2018.01); *H01Q 1/273* (2013.01); *H01Q 15/0093* (2013.01); *G08C 2201/50* (2013.01); *H02J 50/20* (2016.02)

(58) Field of Classification Search
CPC .............. A61N 1/0534; A61N 1/36125; A61N 1/36128; A61N 1/3787; G16H 20/40; H02J 50/20; G08C 2201/50
See application file for complete search history.

(56) References Cited

U.S. PATENT DOCUMENTS

| | | | | |
|---|---|---|---|---|
| 6,414,835 B1 * | 7/2002 | Wolf | ..................... | A61N 1/3754 361/302 |
| 6,415,184 B1 * | 7/2002 | Ishikawa | ............... | A61N 1/3605 607/45 |
| 6,889,084 B2 * | 5/2005 | Thompson | ........... | A61N 1/3758 607/2 |
| 7,012,327 B2 * | 3/2006 | Huff | ......................... | H01G 5/16 257/686 |
| 7,164,572 B1 * | 1/2007 | Burdon | ................ | A61N 1/3754 361/302 |

(Continued)

*Primary Examiner* — Christopher A Flory
(74) *Attorney, Agent, or Firm* — Holland & Hart LLP

(57) ABSTRACT

Methods, systems, and devices for wireless signal transmission are described. A fractal antenna may be utilized to wirelessly communicate with a transmitter implanted within or located external to the patient. The fractal antenna may be implanted within the patient and may be coupled with a lead also implanted within the patient. The characteristics of the fractal antenna may allow for enhanced data transmission between the antenna and the transmitter while reducing the need for implanted wires to connect the transmitter and leads.

18 Claims, 12 Drawing Sheets

(56) References Cited

U.S. PATENT DOCUMENTS

| | | | |
|---|---|---|---|
| 7,317,946 B2* | 1/2008 | Twetan | A61N 1/37229 128/903 |
| 7,904,170 B2 | 3/2011 | Harding | |
| 8,369,950 B2* | 2/2013 | Rawat | A61N 1/37512 607/32 |
| 8,731,668 B2* | 5/2014 | Rawat | A61N 1/37518 607/32 |
| 9,093,741 B1* | 7/2015 | Weller | H01Q 9/26 |
| 10,111,643 B2 | 10/2018 | Schulhauser et al. | |
| 2003/0011515 A1* | 1/2003 | Warble | H01Q 25/00 342/372 |
| 2003/0122713 A1* | 7/2003 | Morris | H01Q 1/38 343/700 MS |
| 2004/0008157 A1* | 1/2004 | Brubaker | G02B 27/017 345/8 |
| 2004/0215280 A1* | 10/2004 | Dublin | A61N 1/37229 607/36 |
| 2005/0060011 A1* | 3/2005 | Denker | A61N 1/3787 607/60 |
| 2006/0214855 A1* | 9/2006 | Harada | H01Q 1/38 343/700 MS |
| 2007/0060970 A1* | 3/2007 | Burdon | A61N 1/3754 607/37 |
| 2007/0123949 A1* | 5/2007 | Dabney | H03H 1/0007 607/37 |
| 2007/0238496 A1* | 10/2007 | Chung | H04B 5/0043 455/575.7 |
| 2008/0021522 A1* | 1/2008 | Verhoef | H01Q 1/36 607/60 |
| 2008/0036668 A1* | 2/2008 | White | H01Q 1/38 343/745 |
| 2008/0195180 A1* | 8/2008 | Stevenson | A61N 1/05 607/60 |
| 2009/0046028 A1* | 2/2009 | Han | H01Q 21/28 343/787 |
| 2009/0182388 A1* | 7/2009 | Von Arx | A61N 1/37282 607/5 |
| 2009/0228074 A1* | 9/2009 | Edgell | H01Q 1/36 607/60 |
| 2010/0100157 A1* | 4/2010 | Nghiem | A61N 1/37229 607/60 |
| 2010/0109958 A1* | 5/2010 | Haubrich | H01Q 1/38 343/718 |
| 2010/0109966 A1* | 5/2010 | Mateychuk | H01Q 1/38 343/841 |
| 2010/0114245 A1* | 5/2010 | Yamamoto | H01Q 21/28 607/60 |
| 2010/0114246 A1* | 5/2010 | Yamamoto | A61N 1/37223 607/60 |
| 2010/0168817 A1* | 7/2010 | Yamamoto | H01Q 3/26 607/60 |
| 2010/0168818 A1* | 7/2010 | Barror | A61N 1/37512 607/60 |
| 2011/0213208 A1* | 9/2011 | McKenna | H02J 50/402 600/300 |
| 2011/0307284 A1 | 12/2011 | Thompson et al. | |
| 2012/0067872 A1* | 3/2012 | Libman | H05B 6/666 219/702 |
| 2012/0283800 A1* | 11/2012 | Perryman | A61N 1/36125 607/60 |
| 2013/0131752 A1* | 5/2013 | Rawat | A61N 1/37518 607/32 |
| 2013/0253612 A1* | 9/2013 | Chow | H02J 50/20 607/60 |
| 2014/0058481 A1* | 2/2014 | Perryman | A61N 1/3708 607/62 |
| 2014/0249612 A1* | 9/2014 | Bonmassar | C09K 19/3809 607/116 |
| 2015/0380355 A1* | 12/2015 | Rogers | H01L 29/78603 257/773 |
| 2016/0331960 A1* | 11/2016 | Katnani | A61N 1/0534 |
| 2016/0367825 A1* | 12/2016 | Perryman | A61N 1/37235 |
| 2017/0036033 A9* | 2/2017 | Perryman | A61N 1/37258 |
| 2017/0365557 A1* | 12/2017 | Rogers | H01L 23/538 |
| 2019/0126043 A1* | 5/2019 | Cullen | A61N 5/0601 |
| 2019/0240476 A1 | 8/2019 | Harding et al. | |
| 2020/0251811 A1* | 8/2020 | Elghannai | H01Q 1/273 |
| 2020/0268256 A1 | 8/2020 | Harding et al. | |
| 2020/0410176 A1 | 12/2020 | Hinrichsen et al. | |

* cited by examiner

PASSIVE PROPAGATION FRACTAL ANTENNA FOR INTRABODY TRANSMISSIONS

BACKGROUND

The following relates generally to wireless signal transmission, and more specifically to a passive propagation fractal antenna for intrabody transmissions of signals.

In a healthcare facility such as a hospital, physiological parameters of the patient (e.g., heart rate, respiratory rate, blood pressure) may be monitored by one or more medical devices. The medical devices may be battery powered and may wirelessly transmit measured patient data over a wireless network within the hospital, thereby allowing the patient to move freely through the hospital while being monitored. Clinicians may remotely monitor the patient by accessing the patient data at a central nurse station or on any web enabled device connected to the network (e.g., smartphone or tablet).

In some cases, implantation of a medical device may involve surgically implanting multiple leads within a patient. For example, to implant a deep brain stimulation device, one or more leads may be implanted intracranially, and a corresponding transmitter may be implanted in another portion of the patient's body (e.g., in the patient's chest). The stimulation device and the transmitter may be connected by one or more wires that are tunneled through the patient's body. Due to the medical devices being implanted in different portions of the patient's body, and the related surgical time associated with implanting the medical devices and the connecting wires, patients may be subjected to multiple invasive and time consuming procedures.

SUMMARY

The described features generally relate to methods, systems, devices, or apparatuses that support passive propagation fractal antenna for wireless transmission of signals. A system for wireless signal transmission is described. In some examples, the system may include a fractal antenna configured to be affixed cranially on a patient, one or more leads coupled with the fractal antenna and configured for implantation in the patient, wherein the one or more leads are configured to deliver an electrical or electromagnetic signal to the patient, and a transmitter in wireless communication with the fractal antenna, wherein the transmitter is configured to wirelessly transmit a control signal relating to the electrical or electromagnetic signal to the fractal antenna, wherein the one or more leads are configured to deliver the electrical or electromagnetic signal to the patient based at least in part on the fractal antenna receiving the control signal.

In some examples, the system may include a central processing unit (CPU) coupled with the fractal antenna, wherein the CPU is configured to process the received control signal. In some examples, the one or more leads are further configured to receive biometric data associated with the patient. In some examples, the CPU is configured to process the biometric data associated with the patient for transmission via the fractal antenna. In some examples, the CPU is configured to authenticate the transmitter and the fractal antenna based at least in part on receiving the control signal.

In some examples, the CPU comprises a radio frequency (RF) chip, and wherein the control signal comprises a RF signal. In some examples, the RF chip is configured to convert the RF signal into a power source or an energy source for the fractal antenna, the one or more leads, or both. In some examples, the electrical or electromagnetic signal is configured for deep brain stimulation. In some examples, the fractal antenna comprises circuitry that is configured to power on based at least in part on receiving the control signal from the transmitter. In some examples, the transmitter is configured for subcutaneous implantation. In some examples, the fractal antenna comprises a flexible structure.

A method for wireless signal transmission is described. In some examples, the method may include receiving, at a fractal antenna configured to be affixed cranially on a patient, a control signal from a transmitter in wireless communication with the fractal antenna, determining, at the fractal antenna, an electrical or electromagnetic therapy operation to be performed on the patient based at least in part on receiving the control signal, and transmitting, to one or more leads coupled with the fractal antenna, a second control signal to perform the electrical or electromagnetic therapy operation on the patient.

In some examples, the method may include receiving, at a central processing unit (CPU) coupled with the fractal antenna, feedback from the one or more leads, the feedback being associated with the electrical or electromagnetic therapy operation and transmitting the feedback via the fractal antenna. In some examples, the electrical or electromagnetic therapy operation comprises deep brain stimulation or neuro stimulation. In some examples, the received control signal is configured to power the fractal antenna, the one or more leads, or both.

In some examples, the control signal comprises a radio frequency (RF) signal. In some examples, the fractal antenna and the one or more leads are configured for subcutaneous implantation. In some examples, the fractal antenna comprises at least one self-similar design.

An apparatus for wireless signal transmission is described. In some examples, the apparatus may include a fractal antenna configured to be affixed cranially on a patient, wherein the fractal antenna is configured to receive a control signal and a central processing unit (CPU) coupled with the fractal antenna and configured for implantation in the patient. In some examples, the CPU may be configured to determine an electrical or electromagnetic therapy operation to be performed on the patient based at least in part on receiving the control signal and transmit, to one or more leads coupled with the fractal antenna, a second control signal to perform the electrical or electromagnetic therapy operation on the patient.

In some examples, the CPU may be configured to determine thermal feedback associated with the fractal antenna, the one or more leads, or both, and transmit an indication of the thermal feedback via the fractal antenna. In some examples, the CPU may be configured to convert the control signal into a power source for the fractal antenna, the one or more leads, or both. In some examples the control signal comprises a radio frequency (RF) signal, and wherein the CPU comprises a RF chip configured to receive the RF signal. In some examples, the fractal antenna comprises at least one self-similar design.

An apparatus for wireless signal transmission is described. In some examples, the apparatus may include a fractal antenna configured to be affixed cranially on a patient and one or more leads coupled with the fractal antenna and configured for implantation in the patient, wherein the one or more leads are configured to deliver an electrical or electromagnetic signal to the patient based at least in part on control signals received by the fractal antenna.

In some examples, the one or more leads are further configured to receive biometric data associated with the patient and communicate the biometric data to the fractal antenna. In some examples, the fractal antenna is configured to wirelessly transmit feedback associated with the electrical or electromagnetic signal. In some examples, the one or more leads are configured for intercranial implantation in the patient.

In some examples, the fractal antenna and the one or more leads each comprise a bio-inert coating. In some examples, the fractal antenna is configured to receive a multi-band or wide-band radio frequency (RF) signal. In some examples, the fractal antenna comprises at least one self-similar design.

DETAILED DESCRIPTION

Figure 1:
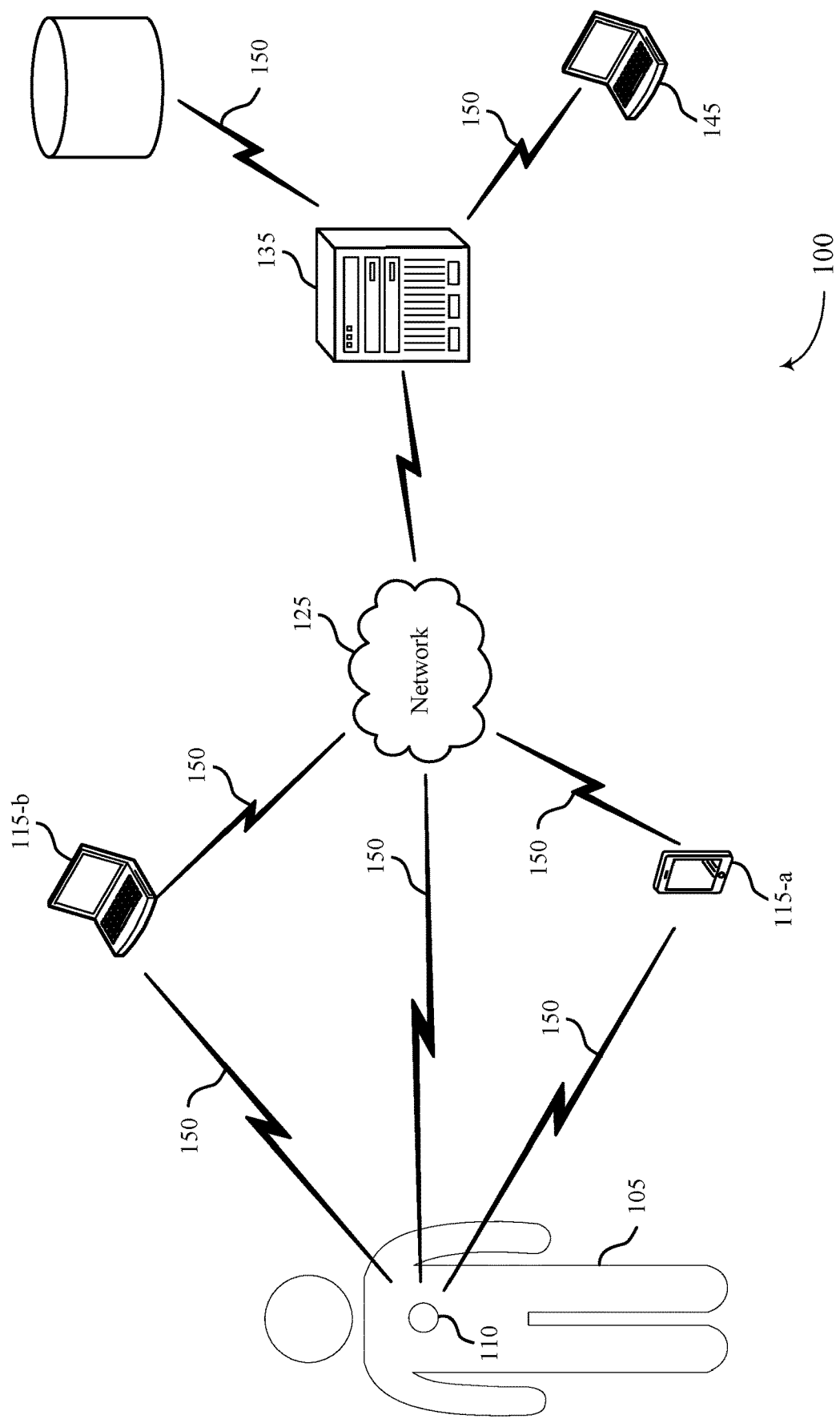
FIG. 1 illustrates an example of a system for intrabody wireless signal transmission that supports a passive propagation fractal antenna for intrabody transmissions in accordance with aspects of the present disclosure.

When performing medical procedures, intrabody device-to-device data transmissions ordinarily utilize various device leads located throughout a patient's body. For example, when performing neuro and/or cardiac procedures, leads may be placed throughout the patient's body and may be coupled with stimulators implanted within the patient. Each stimulator may be responsible for activating a respective lead (e.g., transmitting a signal to the lead) in order to perform a related procedure (e.g., an electrotherapy procedure). However, in order to implant various leads and/or stimulators within a patient's body, the patient may often undergo multiple medical procedures. For example, a patient may undergo a procedure to implant one or more intercranial leads, and may undergo a subsequent procedure to implant a stimulator to communicate with the intercranial leads, and in some cases undergo yet another procedure to implant wires that connect the intercranial leads to the stimulator. Thus a system capable of reducing an amount of leads and/or devices (e.g., stimulators) within a patient's body may reduce an amount of procedures that a patient is subjected to. By reducing a number of procedures that a patient is subjected to, a number of risk factors associated with each unperformed procedure may also be reduced.

In order to reduce an amount of leads and/or devices implanted within a patient's body, a fractal antenna coupled with a lead may be implanted within a patient. A fractal antenna may be an antenna that uses a fractal, self-similar design to maximize the length, or increase the perimeter of material that can receive or transmit electromagnetic radiation within a given total surface area or volume. Fractal antennas may be compact in size, and may utilize multiband and/or wideband signaling. Compared with traditional antenna designs, a fractal antenna may be capable of operating at a high level on a multitude of frequencies simultaneously. Accordingly, fractal antennas may be smaller in size than traditional antennas, yet still provide optimum performance. The reduction in size (e.g., as compared with traditional antenna designs) may allow for a fractal antenna to be implanted within a patient using less-intrusive surgical methods.

In some examples, a fractal antenna may be coupled with a lead that may be implanted within a patient. For example, a lead may be implanted within a patient's skull and may be placed and configured for deep brain stimulation. The fractal antenna may be coupled with the lead and may be located, for example, on the exterior of the patient's skull (but under the skin). Because the antenna may wirelessly receive one or more signals from a device that is implanted or external to the patient (e.g., from a transmitter), the patient may experience reduced surgical time and associated medical issues related to infection and/or tissue damage due to having multiple internally-implanted devices or wires running through the body.

In some examples, the fractal antenna described herein may be configured to communicate both with a lead and a device external to the patient. For example, the antenna may receive signaling (e.g., from a user device of a clinician) indicating that the lead should perform a medical operation (e.g., an intercranial stimulation). Based on receiving the signal, the fractal antenna may convey signaling to the lead to perform the medical operation. In some examples, the fractal antenna may communicate with various external devices and may transmit feedback (e.g., to a user device of the clinician). For example, the fractal antenna may provide for a body mesh (e.g., a full-body monitoring) which may provide wholistic patient health data. Thus, in addition to reducing a number of leads, intrabody devices, and surgical procedures, the use of a fractal antenna may provide for more effective medical operations and patient monitoring.

Aspects of the disclosure are initially described in the context of a wireless patient monitoring system. Aspects of the disclosure are further illustrated by and described with reference to apparatus diagrams, system diagrams, and flowcharts that relate to intrabody wireless transmissions.

FIG. 1 illustrates an example of a wireless patient monitoring system 100 in accordance with various embodiments of the present disclosure. The wireless patient monitoring system 100 may include a patient 105 wearing, carrying, or otherwise coupled with a medical device 110. Although a single medical device 110 is shown, multiple medical devices 110 may be coupled to the patient 105. The patient 105 may be a patient in a hospital, nursing home, home care, a medical facility, or another care facility. The medical device 110 may transmit signals via wireless communications links 150 to computing devices 115 or to a network 125.

The medical device 110 may include one or more sensors configured to collect a variety of physiological parameters as well as information related to the location and movement of the patient 105. For example, the medical device 110 may include a pulse oximetry (SpO2) sensor, a capnography sensor, a heart rate sensor, a blood pressure sensor, an electrocardiogram (ECG) sensor, a respiratory rate sensor, a glucose level sensor, a depth of consciousness sensor, a body temperature sensor, an accelerometer, a global positioning sensor, a sensor which triangulates position from multiple local computing devices 115, or any other sensor configured to collect physiological, location, or motion data associated with the patient 105.

The medical device 110 may include leads, circuitry, and a processor configured to deliver therapeutic energy or stimulation to the patient 105. For example, the medical device 110 may include a deep brain stimulation device.

The medical device 110 may be coupled with the patient 105 in a variety of ways depending on the data being collected. For example, the medical device 110 may be directly coupled with the patient 105 (e.g., physically connected to the patient's chest, worn around the patient's wrist, attached to the patient's finger, or positioned over the patients nose or mouth). In some cases, the medical device 110 may implanted within the patient 105 (e.g., in the skull or chest of the patient 105). The data collected by the medical device 110 may be wirelessly transmitted to either the computing devices 115 or to the remote computing device 145 (via the network 125 and central station 135). Data transmission may occur via, for example, frequencies appropriate for a personal area network (such as Bluetooth, Bluetooth Low Energy (BLE), or IR communications) or local (e.g., wireless local area network (WEAN)) or wide area network (WAN) frequencies such as radio frequencies specified by IEEE standards (e.g., IEEE 802.15.4 standard, IEEE 802.11 standard (Wi-Fi), IEEE 802.16 standard (WiMAX), etc., or evolutions of those wireless standards).

Computing device 115-a may be a wireless device such as a tablet, cellular phone, personal digital assistant (PDA), a dedicated receiver, or other similar device or a spatially distributed network of devices configured to receive signals from the medical device 110. Computing device 115-b may be a wireless laptop computer, a clinician Workstation on Wheels, or a smart hospital bed configured to receive signals from the medical device 110. The computing devices 115 may be in communication with a central station 135 via network 125.

The medical device 110 may also communicate directly with the central station 135 via the network 125. The central station 135 may be a server or a central nurse station located within the hospital or in a remote location. The central station 135 may be in further communication with one or more remote computing devices 145, thereby allowing a clinician to remotely monitor the patient 105. The central station 135 may also be in communication with various remote databases 140 where the collected patient data may be stored. In some cases, the remote databases 140 include electronic medical records (EMR) applications for storing and sharing patient data.

In some examples, a remote computing device 145 may communicate with a medical device 110 associated with the patient 105. The medical device 110 may be directly associated (e.g., implanted within) with the patient 105 and, in some examples, may be a one or more leads. As herein above, the one or more leads may be configured to perform an electrical or electromagnetic therapy operation on the patient 105. In some examples, the remote computing device 145 may be operated by a clinician (not shown) and may communicate with the medical device 110 via an antenna (not shown). For example, a clinician may initiate an electrical or electromagnetic therapy operation to be performed by medical device 110. The remote computing device 145 may transmit a signal to the fractal antenna, which may activate the medical device 110 associated with the patient 105.

As described herein, the use of an antenna coupled with the medical device 110 may reduce a total amount of surgical time that the patient 105 is subjected to. For example, the antenna may be located subdermally (e.g., implanted within the patient 105) and may be coupled with the medical device 110 (e.g., one or more leads). In some examples, both the leads and the antenna may be implanted within the patient 105. The antenna may be in communication with a transmitter that is also implanted or that is external to the patient 105 (e.g., not implanted within the patient 105) and may communicate one or more signals relating to a medical operation. Because the transmitter and the antenna can wirelessly communicate, the patient 105 may avoid additional surgeries to implant the wires that conventionally connect the transmitter to the implanted leads. In some examples, the size of the antenna (e.g., a smaller size as compared with traditional antenna designs) may allow for the fractal antenna to be implanted within a patient using less-intrusive surgical methods.

In some examples, the use of an antenna coupled with one or more leads may replace existing methods for device to device (D2D) data bridging and intrabody signals transmission by receiving communications external to the patient 105 and implementing them using an implanted medical device 110. In some examples, the system may include one or more low power bio-inert fractal antennas and an embedded programmable processing module that may enable implanted medical devices to transmit device and/or sensor signals within a biological environment. Thus, in addition to reducing a number of leads, intrabody devices, and surgical procedures, the use of an antenna coupled with one or more leads may provide for more effective medical operations and patient monitoring.

Figure 2:
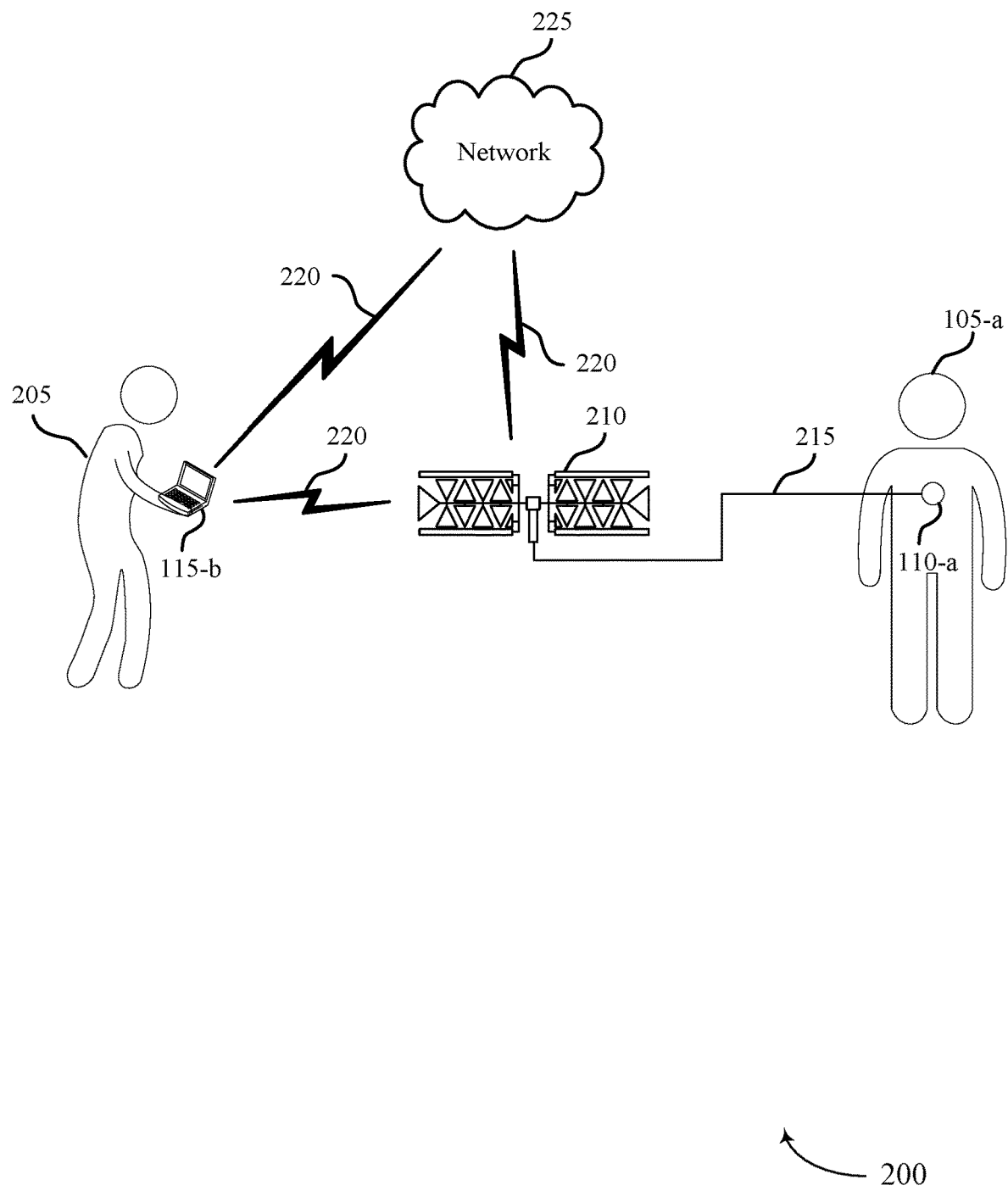
FIG. 2 illustrates an example of a system that supports a passive propagation fractal antenna for intrabody transmissions in accordance with aspects of the present disclosure.

FIG. 2 illustrates an example of a system 200 that supports a passive propagation fractal antenna for intrabody transmissions in accordance with aspects of the present disclosure. The system 200 may be an example of aspects of the system 100 and may include a patient 105-a wearing, carrying, or otherwise coupled with a medical device 110-a. The medical device 110-a may be an example of medical device 110 as described with reference to FIG. 1, and may include one or leads configured to perform a medical operation (e.g., an electrical or electromagnetic therapy operation) on the patient 105-a. In some examples, the system 200 may also include a clinician 205; a user device 115-h, which may be an example of computing device 115-a or 145 as described with reference to FIG. 1; an antenna 210; and a network 225, which may be an example of network 125 as described with reference to FIG. 1. In some examples, the antenna 210 may be coupled with the medical device 110-*a* via one or more leads 215. Each of the components illustrated may be connected via communication links 220, which may be examples of communication links 150 as described with reference to FIG. 1.

In some examples, the user device 115-*b* may be configured to transmit one or more signals to the antenna 210. For example, a user of user device 115-*b* may include a doctor, a nurse, a physician assistant, or a technician. The user may, for example, indicate to the user device 115-*b* a medical operation to be performed on the patient 105-*a*. In some examples, the medical operation may be or may be associated with an electrical or electromagnetic therapy operation, such as a deep brain stimulation and/or a neuro or cardiac therapy operation. In some examples, the antenna 210 may authenticate the user device 115-*b*. Stated another way, if a user (e.g., clinician 205) of the user device 115-*b* possesses the requisite credentials, the antenna may authenticate the user device 115-*h* upon receiving a signal from the user device 115-*b*. For example, a user device 115-*b* may be required to possess doctor-level credentials in order for the medical operation to be performed on the patient 105-*a*. As described herein, the antenna 210 may authenticate the user device 115-*b* based on one or more credentials of the clinician 205 and/or a characteristic of the signal received. The signal may be transmitted directly to the antenna 210 via communication link 220 or, in other examples, may be transmitted via communication link 220 by way of network 125-*a*.

In some examples, the antenna 210 may be in communication with the user device 115-*b* (e.g., a transmitter). The user device 115-*b* may be configured to communicate with the antenna 210, and wirelessly transmit a control signal relating to an electrical or electromagnetic therapy operation to the antenna 210. Because the user device 115-*b* may be located external to the patient 105-*a* and may be utilized to communicate with one or more leads 215 via the antenna 210, the patient 205 may be subjected to fewer medical procedures. Stated another way, the antenna 210 may be coupled with the one or more leads 215, which may be implanted within the patient 105-*a*. The antenna 210 may receive one or more signals (e.g., an RF signal) from the user device 115-*b* (e.g., via communication link 220 or via communication link 220 by way of network 225) and subsequently transmit a signal to the one or more leads 215. Due to the one or more signals being received from a device located external to the patient 105-*a* (e.g., front user device 115-*b*), the patient 105-*b* may not need any type of electrical or electromagnetic transmission device implanted within himself or herself. Accordingly, the patient 105-*a* may be subjected to fewer medical procedures and, in turn, may be subject to fewer medical complications.

As described herein, the one or more leads may be coupled with the antenna 210 and may be configured to perform a medical operation on the patient 105-*a*. For example, the one or more leads 215 may be configured to perform an electrical or electromagnetic therapy operation. An electrical or electromagnetic therapy operation may be or may include, for example, a deep brain stimulation operation or a neuro or cardio therapy operation. For example, the one or more leads 215 may be implanted within the patient 105-*a* at an implantation site, and may be associated with a deep brain stimulation operation or a cardio and/or neuro therapy operation. If the one or more leads 215 are associated with a deep brain stimulation operation, the implantation site may be located at or around the patient's 105-*a* head. Additionally or alternatively, if the one or more leads 215 are associated with a cardio therapy operation, the implantation site may be located at or around the patient's 105-*a* chest. In some examples, the one or more leads 215 may include a bio-inert coating such that the one or more leads 215 may be safely implanted within the patient 105-*a*.

In some examples, the one or more leads 215 may be configured to monitor biometric parameters associated with the patient 105-*a* and transmit the information to the clinician 205 (e.g., to the user device 115-*b*). For example, the one or more leads 215 may be able to monitor biometric information such as the patient's 105-*a* heart rate and/or blood pressure. In some examples, the one or more leads 215 may monitor biometric information associated with the electrical or electromagnetic therapy operation. For example, the electrical or electromagnetic therapy operation may be related to or may include a deep brain stimulation operation, and the one or more leads 215 may measure one or more characteristics associated with the patient's 105-*a* brain before, during, and/or after the electrical or electromagnetic therapy operation. As described herein, the biometric information monitored by the one or more leads 215 may be transmitted to the user device 115-*b* using the antenna 210 and communication link 220. In some examples, the biometric information may be transmitted to the user device 115-*h* by way of the network 225.

Figure 3:
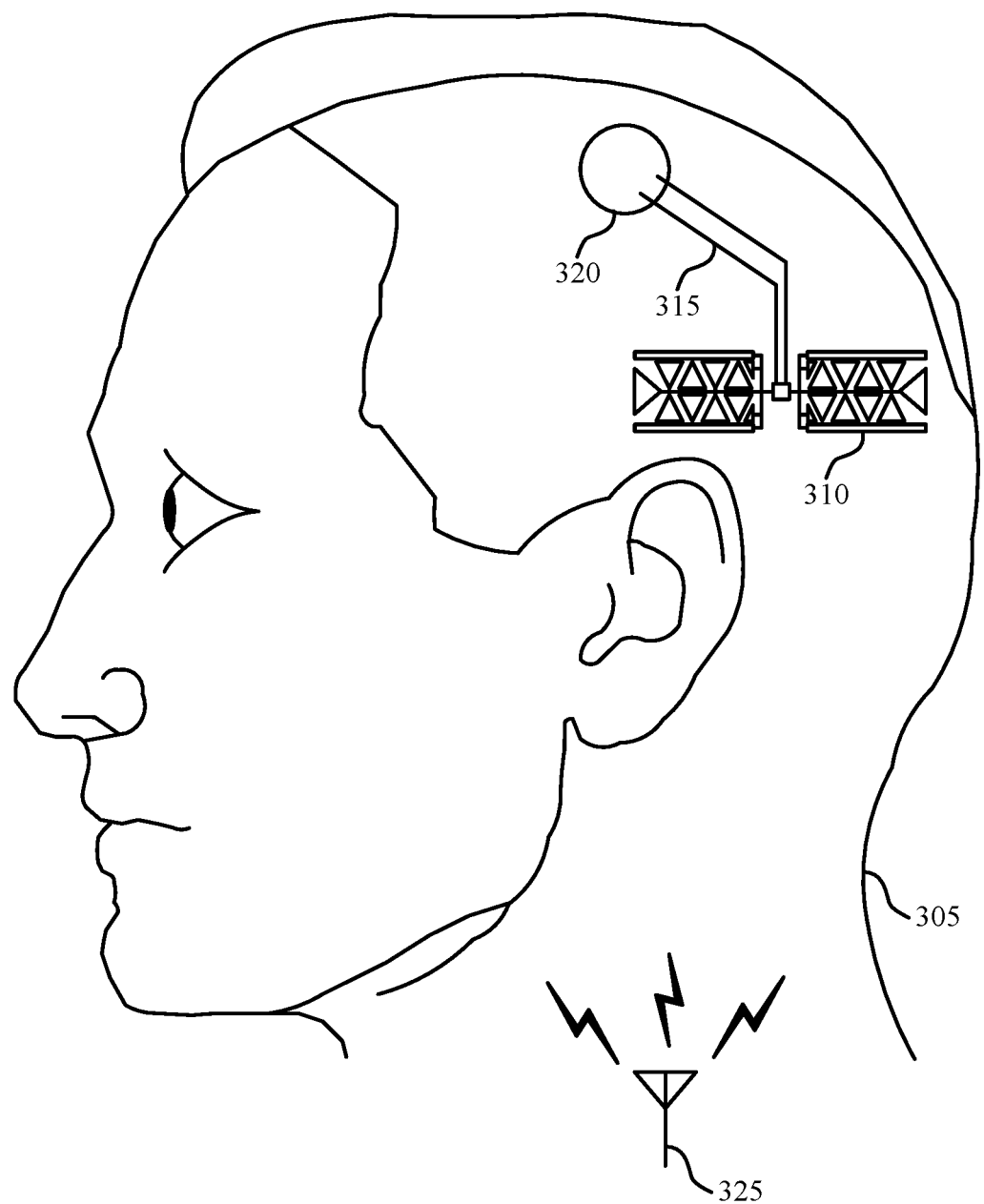
FIG. 3 illustrates an example of an environment that supports a passive propagation fractal antenna for intrabody transmissions in accordance with aspects of the present disclosure.

FIG. 3 illustrates an example of an environment 300 that supports a passive propagation fractal antenna for intrabody transmissions in accordance with aspects of the present disclosure. In some examples, the environment 300 may include a patient 305, an antenna 310, one or more leads 315, an implantation site 320, and a transmitter 325. In some examples, the antenna may be or may be referred to as a fractal antenna, and may be an example of antenna 210 as described with reference to FIG. 2. In some examples, the antenna 310 may communicate with an user device (not shown) that may be associated with, for example, a clinician.

In some examples, the antenna 310 may be utilized to communicate with one or more leads 315 and may be affixed cranially on the patient 305. For example, the antenna 310 and leads 315 may be implanted subcutaneously within the patient 305 and may communicate with a transmitter 325 that is implanted or located external to the patient 305. In some examples, the antenna 310 and/or the leads 315 may be implanted subgaleally in the patient's skull. Stated another way, the antenna 310 and/or the leads 315 may be implanted between the patient's skull periosteum and the scalp galea aponeurosis. By cranially affixing the antenna 310 on the patient 305, the length of the leads 315 may be reduced (e.g., the distance between the antenna 310 and the end of the leads 315 may be reduced) as compared to if the antenna 310 were implanted in the body farther from the patient's skull. Additionally or alternatively, cranially affixing the antenna 310 to the patient 305 may reduce a number of medical procedures otherwise needed to implant antenna and/or transceiver within the patient (e to communicate with the leads 315).

The antenna 310 may receive one or more signals (e.g an RF signal) from the transmitter 325 and subsequently transmit a signal to the one or more leads 315. For example, a user device associated with a clinician may transmit a signal associated with an electrical or electromagnetic therapy operation to the antenna 310 (e.g., via transmitter 325). The antenna 310 may, in some examples, generate a signal and transmit the signal to the one or more leads 315. The signal transmitted to the one or more leads 315 may, in some examples, result in the one or more leads 315 performing the electrical or electromagnetic therapy operation.

In some examples, the transmitter 325 may be located in any location external to the patient 305. For example, the transmitter 325 may be mounted to or worn by the patient or may be located within a same room as the patient 305 (e.g., within a relatively short distance). In other examples, the transmitter 325 may be located in any location such that is able to communicate with the antenna 310 to initiate a medical operation (e.g., an electrical or electromagnetic therapy operation).

In some examples, the antenna 310 may be implanted in any location of the patient's 305 body. Thus the distance that the antenna 310 is located from the implantation site 320 may be proportional to a length of the one or more leads 315. Because the one or more leads 315 may be coupled with the antenna 310, and the one or more leads 315 may be implanted within the patient 305 (e.g., at implantation site 320), the one or more leads 315 may necessarily be longer if the antenna 310 is located farther from implantation site 320.

As described herein, the one or more leads 315 may be coupled with the antenna 310 and may be configured to perform a medical operation on the patient 305. For example, the one or more leads 315 may be configured to perform an electrical or electromagnetic therapy operation. An electrical or electromagnetic therapy operation may be or may include, for example, a deep brain stimulation operation, a neuro or cardio therapy operation, or a vagus nerve stimulation (VNS) therapy operation. For example, the implantation site 320 may represent a location on the patient 305 where the one or more leads 315 are implanted. For example, if the one or more leads 315 are associated with a deep brain stimulation operation, the implantation site 320 may be located at or around the patient's 305 head. Additionally or alternatively, if the one or more leads 315 are associated with a cardio therapy operation, the implantation site 320 may be located at or around the patient's 305 chest. Further, if the one or more leads 315 are associated with a VNS therapy operation, the implantation site 320 may be located at or around the patient's 305 vagus nerve. In some examples, the one or more leads 315 may include a bio-inert coating such that the one or more leads 315 may be safely implanted within the patient 305.

In some examples, the antenna 310 may be configured to receive a control signal (e.g., from a user device associated with a clinician) from the transmitter 325. Thus, upon receiving the control signal, the antenna 310 may be configured to activate the one or more leads 315. In some examples, the control signal may indicate a particular electrical or electromagnetic therapy operation to be conducted. However, in some examples, the control signal may include one or more characteristics and/or identifiers. Thus, when received by the antenna 310, the antenna 310 (e.g., a CPU coupled with the antenna 310) may determine the particular medical operation to perform on the patient 305 (e.g., via the one or more leads 315).

Because the antenna 310 may be configured to receive a control signal from the transmitter 325 and subsequently activate the one or more leads 315 in order to perform a medical operation on the patient 305, the antenna 310 may be located anywhere within the patient 305. However, as described above, in some examples the antenna 310 may be affixed cranially to the patient. By implanting the antenna 310 and leads 315 cranially within the patient 305, the patient 305 may be subjected to fewer operations to implant medical devices since there is no need for a lead wire to extend from the leads 315 to an implanted stimulation controller (e.g., implanted in the patient's chest). Stated another way, implanting a stimulation device within the patient 305 in a location other than the skull area and connecting the stimulation device to the leads 315 with a lead wire may subject the patient 305 to additional surgical procedures. As described herein, because the transmitter 325 is located external to the patient 305 yet still able to communicate with the antenna 310 and one or more leads 315, the patient 305 may experience fewer implantation procedures. Further, fewer medical devices located within a patient 305 may result in reduced failure rates related to breakage, impedance, maintenance requirements, and may reduce patient 305 complications due to infection resulting from the implantation of various devices.

Figure 4:
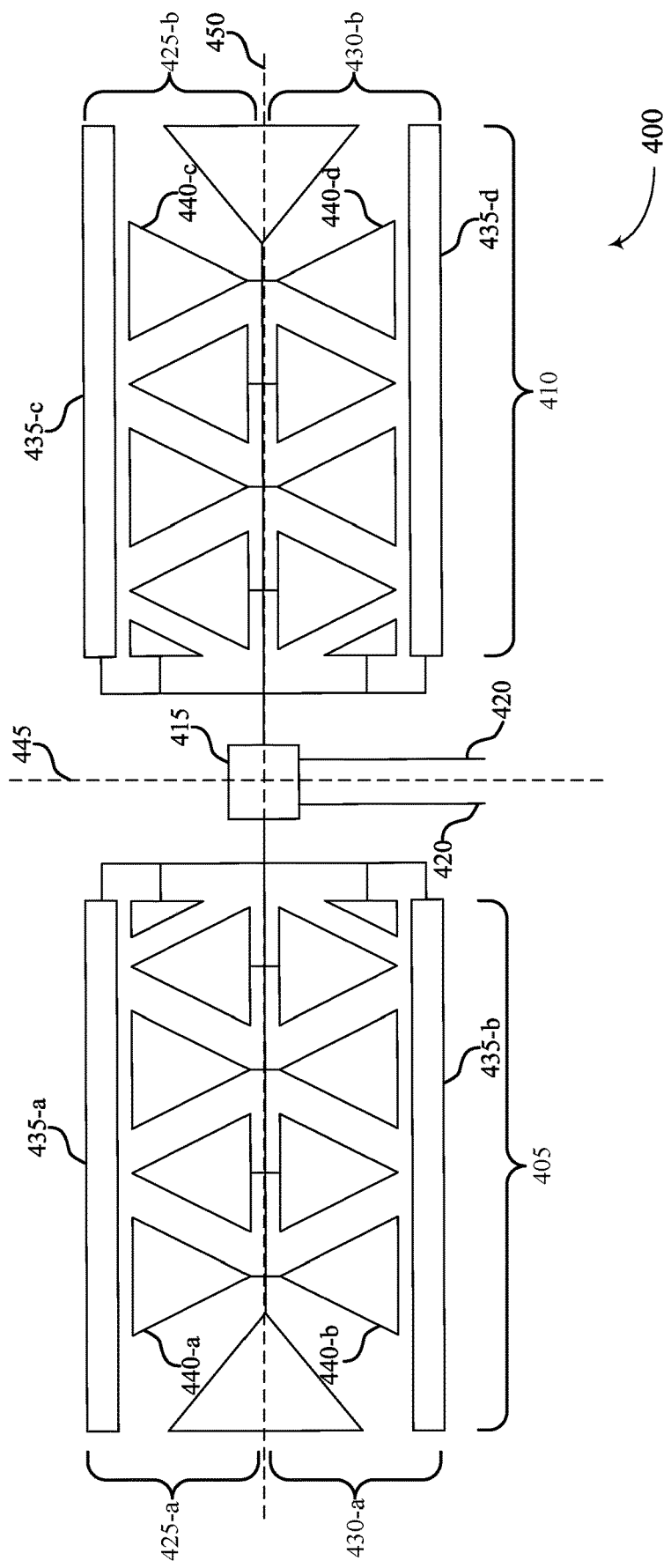
FIG. 4 illustrates an example of an antenna that supports a passive propagation fractal antenna for intrabody transmissions in accordance with aspects of the present disclosure.

FIG. 4 illustrates an example of an antenna 400 that supports a passive propagation fractal antenna for intrabody transmissions in accordance with aspects of the present disclosure. Antenna 400 may be or may be referred to as a fractal antenna, and may be an example of antenna 210 as described with reference to FIG. 2. The antenna 400 may include a first portion 405, a second portion 410, a central processing unit (CPU) 415, and one or more leads 420. In some examples, the antenna 400 may include a self-similar design to maximize its effective length.

The first portion 405 may include a first set of antenna elements. The first portion 405 of the first set of antenna elements may include a first subset of antenna elements 425-a and a second subset of antenna elements 430-a. The first subset of antenna elements 425-a may include antenna elements of a first geometry 435-a and antenna elements of a second geometry 440-a. For example, the first geometry 435-a may be an example of a rectangle, and the second geometry 440-a may be an example of a triangle. Additionally or alternatively, the first geometry may be a triangle of a first shape (e.g., a right triangle), and the second geometry may be a triangle of a second shape (e.g., an isosceles triangle). Additionally or alternatively, the first geometry may be a triangle (or other shape) of a first size, and the second geometry may be a triangle (or other shape) of a second size. In such cases, the first geometry 435-a may be different than the second geometry 440-a.

The second subset of antenna elements 430-a may include antenna elements of a first geometry 435-b and antenna elements of a second geometry 440-b. For example, the first geometry 435-b may be an example of a rectangle, and the second geometry 440-b may be an example of a triangle. In such cases, the first geometry 435-b may be different than the second geometry 440-b.

The second portion 410 may include a second set of antenna elements. The second portion 410 of the second set of antenna elements may include a first subset of antenna elements 425-b and a second subset of antenna elements 430-b. The first subset of antenna elements 425-b may include antenna elements of a first geometry 435-c and antenna elements of a second geometry 440-c. For example, the first geometry 435-c may be an example of a rectangle, and the second geometry 440-c may be an example of a triangle. Additionally or alternatively, the first geometry may be a triangle of a first shape (e.g., a right triangle), and the second geometry may be a triangle of a second shape (e.g., an isosceles triangle). Additionally or alternatively, the first geometry may be a triangle (or other shape) of a first size, and the second geometry may be a triangle (or other shape) of a second size. In such cases, the first geometry 435-c may be different than the second geometry 440-c.

The second subset of antenna elements 430-*b* may include antenna elements of a first geometry 435-*d* and antenna elements of a second geometry 440-*d*. For example, the first geometry 435-*d* may be an example of a rectangle, and the second geometry 440-*d* may be an example of a triangle. In such cases, the first geometry 435-*d* may be different than the second geometry 440-*d*.

In some examples, the antenna 400 may include a self-similar design to increase the perimeter of material that can receive or transmit signals (e.g., an RF signal). This may result in the antenna 400 being both compact and wideband. In some examples, a self-similar design may refer to both the first portion 405 and the second portion 410 being identical. For example, an antenna pattern of the first portion 405 of the first set of antenna elements may be symmetric with an antenna pattern of the second portion 410 of the second set of antenna elements with respect to a first axis 445 (e.g., vertical axis) of the fractal antenna 400. In such cases, the first subset of antenna elements 425-*a* may be identical to the first subset of antenna elements 425-*b*, and the second subset of antenna elements 430-*a* may be identical to the second subset of antenna elements 430-*b*. For example, each of the first portion 405 and the second portion 410 of the antenna 400 may comprise a similar design. In some cases, an antenna pattern of the first subset of antenna elements 425-*a* and the first subset of antenna elements 425-*b* may be symmetric with an antenna pattern of the second subset of antenna elements 430-*a* and the second subset of antenna patterns 430-*b* with respect to a second axis 450 (e.g., horizontal axis) of the fractal antenna 400. In such cases, both the first subset of antenna elements 425-*a* and 425-*b* may be identical to both the second subset of antenna elements 430-*a* and 430-*b*. In some examples, the antenna 400 may include a flexible (e.g., an adaptable) material. The flexibility of the antenna 400 may allow it to, for example, conform to the curvature of a patient's skull or other body part.

In some examples, the wideband capabilities of the antenna 400 may allow for the antenna 400 to change frequency in response to interference (e.g., radio interference). For example, the antenna 400 may include a Dynamic Channel Selection (DCS), that ensures a steady and reliable link quality (e.g., between the antenna 400 and a transmitter (e.g., a transmitter 325 as described with reference to FIG. 3). In some examples, the DCS may enable the antenna 400 to continuously detect interferences on the current operating channel and seamlessly switch to other interference-free channels. This may result in the antenna 400 experiencing minimal performance degradation.

In some examples, the antenna 400 may support communication protocols that use wider (e.g., as compared with a traditional antenna) frequency ranges. For example, the antenna 400 may support multiple protocols such as 802.11ad in order to provide higher data throughput and lower latency. In some examples, the antenna 400 may operate in less-crowded spectrum bands by operating in the 60 GHz millimeter wave band. The 60 GHz spectrum band may accommodate ultra-wideband channels that enable multiple Gigabit-per-second data rates.

The properties of the antenna 400 may allow for it to have many different resonances, meaning it will act as an antenna for many different electromagnetic frequencies. In some examples, the different resonances may result from the first portion 405 and the second portion 410 acting as a virtual network of capacitors and inductors. In some examples, the antenna 400 may differ from traditional antenna designs (e.g., non-fractal antennas), in that the antenna 400 may be capable of operating with good-to-excellent performance at many different frequencies simultaneously. Standard antennas (e.g., non-fractal antennas) may have to be "cut" for the frequency for which they are to be used and thus the standard antennas only work well at one particular frequency.

In some examples, the antenna 400 may receive one or more signals from an external device (e.g., from a user device associated with a clinician). The signals may be received by CPU 415, which may include one or more processors. In some examples, the CPU 415 may be configured to receive and/or process a control signal received by the antenna 400. The control signal may, as described herein, relate to an electrical or electromagnetic signal to be delivered to a patient. In some examples, the control signal may include identifying characteristics that may be used for authentication purposes. Thus, in some examples, the CPU 415 may authenticate the identifying characteristics such that the one or more leads 420 may deliver a resulting electrical or electromagnetic signal to the patient.

In some examples, the CPU 415 may include a radio frequency (RF) chip and/or a transmitter for transmitting one or more signals via the antenna 400. The CPU 415 may include an RF chip such that, if the antenna 400 receives an RF signal, the CPU 415 may be configured to decipher the signal. Additionally or alternatively, the RF chip may be configured to convert the received RF signal into a power or energy source to power the antenna 400 and/or the one or more leads 420. In some examples, the CPU 415 may include a transmitter in order to transmit one or more signals via the antenna 400. As described herein, the one or more leads 420 may be configured to receive biometric information related to a patient (e.g., due to being implanted within a patient). The one or more leads 420 may transmit the biometric information to the CPU 415 (e.g., to the transmitter), which may transmit the information using the antenna 400. In some examples, the biometric information may be transmitted (e.g., using the antenna 400) to a clinician associated with the patient.

In some examples, the antenna 400 may be fabricated at a nano-scale. Stated another way, the antenna 400 may be fabricated as or on a relatively small circuit board (e.g., a nano-sized circuit board) to facilitate implantation into the body (e.g., within the cranial cavity). The relatively small size of the antenna 400 may, for example, allow versatility in its use with other wireless devices. For example, in a medical environment as described herein, the antenna 400 may support Digital Signal Processing (DSP). Accordingly, the antenna 400 may be fabricated on a dedicated ASIC, FPGA, GPU, and/or DSP chip, and/or may include an embedded processor with DSP extensions. In some examples, the antenna 400 may include a SoC (System-on-Chip) architecture that is based on a FPGA (Field-Programmable Gate Array) medical device solution (e.g., that is suitable for the implementation of biomedical signal processing).

Figure 5:
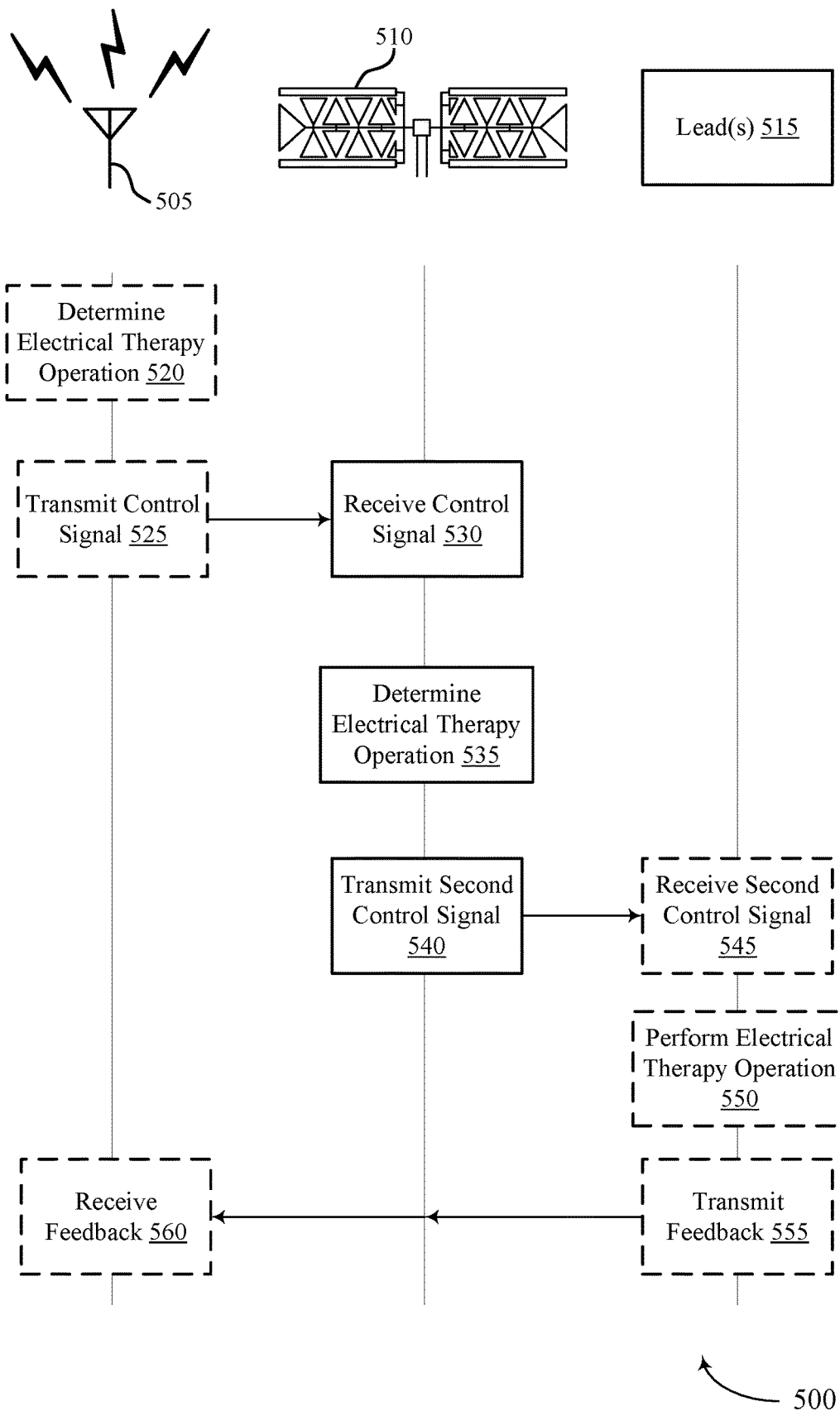
FIG. 5 illustrates an example of a flow diagram that supports a passive propagation fractal antenna for intrabody transmissions in accordance with aspects of the present disclosure.

FIG. 5 illustrates an example of a process flow 500 that supports a passive propagation fractal antenna for intrabody transmissions in accordance with aspects of the present disclosure. Process flow 500 may include transmitter 505, antenna 510, and one or more leads 515. In some examples, the transmitter 505 may be an example of a user device 115-*h* as described with reference to FIG. 2. Additionally or alternatively, antenna 510 may be or may be referred to as a fractal antenna. Alternative examples of the following may be implemented, where some steps are performed in a different order or not at all. Some steps may additionally include additional features not mentioned above.

Transmitter 505 may communicate with antenna 510 via one or more communication links (e.g., a communication link 150 as described with reference to FIG. 1). In some examples, the antenna 510 and one or more leads 515 may be associated with a patient. For example, the one or more leads 515 may be implanted within a patient, and the transmitter 505 may communicate with the one or more leads 515 (e.g., via the antenna 510) in order to perform a medical operation. In some examples, the medical operation may be or may be associated with an electrical or electromagnetic therapy operation. For example, an electrical or electromagnetic therapy operation may include a deep brain stimulation or a neuro stimulation operation (e.g., of the patient). At block 520, the transmitter 505 may determine a particular electrical or electromagnetic therapy operation to be performed on a patient. In some examples, the determination may be made by a clinician. The determination may be made based on one or more input parameters received from a clinician. For example, a clinician may input one or more parameters into a mobile device, which may communicate with the transmitter 505. In some examples, the clinician may make the determination of a particular electrical or electromagnetic therapy operation to be performed, and the electrical or electromagnetic therapy operation may be communicated to the transmitter 505 (e.g., via a mobile device of the clinician).

At block 525, the transmitter 505 may transmit a control signal to the antenna 510. As described herein, the transmitter 505 may determine (e.g., via receiving input from a clinician) an electrical or electromagnetic therapy operation to be performed on a patient. Thus the transmitter 505 may generate a control signal based on the determined operation, and may transmit the control signal to the antenna 510. In some examples, the control signal may indicate to the antenna 510 what operation to be performed on the patient (e.g., via the one or more leads 515). At block 530, the antenna 510 may receive the control signal. In some examples (not shown), the antenna 510 may subsequently generate one or more signals to be communicated to the one or more leads 515 to indicate the particular operation to be performed.

At block 535, the antenna 510 may determine an electrical or electromagnetic therapy operation to be performed. As described herein, in some examples the determination may be made by the transmitter 505. However, in some examples, the control signal transmitted by the server may include a power signal to power-on the antenna 510, or may include one or more parameters associated with the patient. Thus, upon powering-on, the antenna 510 may determine an electrical or electromagnetic therapy operation to be performed.

At block 540, the antenna 510 may transmit a second control signal to the one or more leads 515. As described herein, the antenna 510 may determine (e.g., via receiving a control signal from the transmitter 505) an electrical or electromagnetic therapy operation to be performed on a patient. Thus the antenna 510 may generate a second control signal based on the determined operation, and may transmit the second control signal to the one or more leads 515. In some examples, the second control signal may indicate to the one or more leads 515 what operation to be performed on the patient. At block 545, the one or more leads 515 may receive the second control signal.

At block 550, the one or more leads 515 may perform the determined electrical or electromagnetic therapy operation on the patient. As described herein, the one or more leads 515 may be implanted within a patient. For example, the one or more leads 515 may be implanted within a patient's skull (e.g., intracranially), and the electrical or electromagnetic therapy operation may be or may include a deep brain stimulation operation. In some examples, the one or more leads 515 may be implanted within a different portion or organ of a patient's body, and the electrical or electromagnetic therapy operation may be or may include a different operation (e.g., a neuro stimulation operation).

At block 555, upon performing the determined electrical or electromagnetic therapy operation, the one or more leads 515 may transmit feedback from the operation to the antenna 510. In some examples, the one or more leads 515 may transmit the feedback to the clinician (which may transmit the feedback to a clinician) via the antenna 510. The feedback may relate to the particular operation performed. For example, if the one or more leads 515 performed a deep brain stimulation operation, the one or more leads 515 may facilitate to monitor one or more parameters associated with the stimulation of the patient's brain, and subsequently transmit the data to the transmitter 505 (via the antenna 510). At block 550, the feedback may be received by the transmitter 505.

Figure 6:
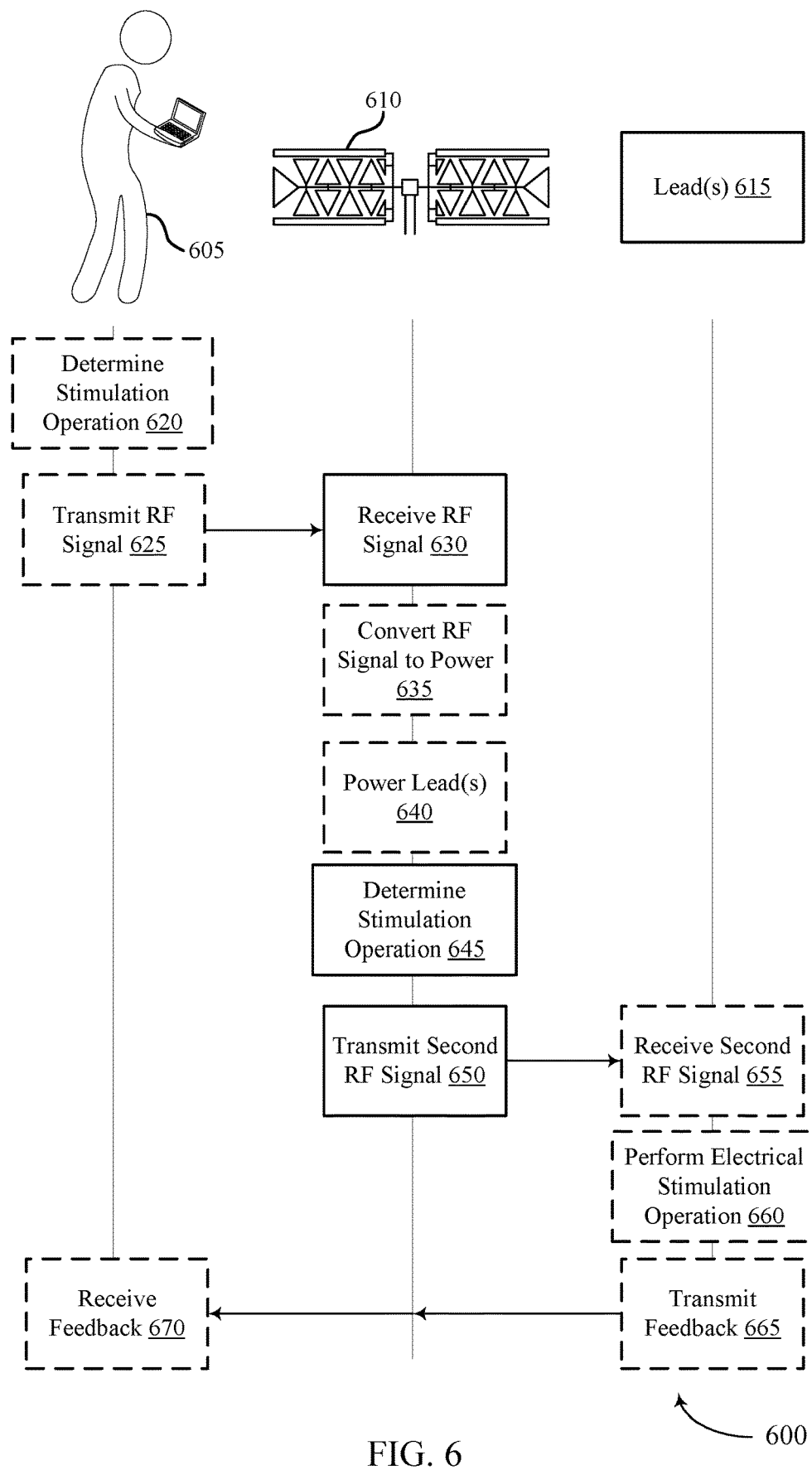
FIG. 6 illustrates an example of a flow diagram that supports a passive propagation fractal antenna for intrabody transmissions in accordance with aspects of the present disclosure.

FIG. 6 illustrates an example of a process flow 600 that supports a passive propagation fractal antenna for intrabody transmissions in accordance with aspects of the present disclosure. Process flow 600 may include clinician 605, antenna 610, and one or more leads 615. In some examples, the clinician 605 may be an example of a clinician 205 as described with reference to FIG. 2. Additionally or alternatively, antenna 610 may be or may be referred to as a fractal antenna. Alternative examples of the following may be implemented, where some steps are performed in a different order or not at all. Some steps may additionally include additional features not mentioned above.

Clinician 605 may communicate with antenna 610 using a user device (not shown) configured to communicate via one or more communication links (e.g., a communication link 150 as described with reference to FIG. 1). In some examples, the antenna 610 and one or more leads 615 may be associated with a patient. For example, the one or more leads 615 may be implanted within a patient, and the clinician 605 may communicate with the one or more leads 615 (e.g., via the antenna 610) in order to perform a medical operation. In some examples, the medical operation may be or may be associated with an electrical or electromagnetic therapy operation. For example, an electrical or electromagnetic therapy operation may include a deep brain stimulation or a neuro stimulation operation (e.g., of the patient). At block 620, the clinician 605 may determine a particular stimulation operation to be performed on a patient. The determination may be made based on one or more health parameters associated with the patient (e.g., determined by the clinician). For example, during a medical procedure, the clinician 605 may determine to perform a deep brain stimulation procedure on the patient. In some examples, the clinician may indicate the determined stimulation operation via a user device, At block 625, the clinician 605 may transmit a radio frequency (RF) signal to the antenna 610. In some examples (not shown), the RF signal may be transmitted to the antenna 610 via a user device of the clinician 605. As described herein, the clinician 605 may determine a stimulation operation to be performed on a patient based on one or more characteristics associated with the patient (e.g., diagnose), or based on a particular procedure being performed on the patient. Thus the clinician 605 (e.g., a user device associated with the clinician) may generate an RF signal based on the determined operation, and may transmit the RF signal to the antenna 610. An RF signal described herein may refer to a signal having one or more oscillating radio waves. For example, an RF signal may refer to a signal having a rate of oscillation of electromagnetic radio waves in the range of 3 kHz to 300 GHz. Additionally or alternatively, an RF signal may include any alternating currents carrying radio signals. In some examples, the RF signal may indicate to the antenna 610 what operation to be performed on the patient (e.g., via the one or more leads 615). At block 630, the antenna 610 may receive the RF signal. In some examples (not shown), the antenna 610 may subsequently generate one or more signals (e.g., one or more RF signals) to be communicated to the one or more leads 615 to indicate the particular operation to be performed.

At block 635, antenna 610 may convert the received RF signal into a power source or an energy source. In some examples, the power and/or energy may be used to power the antenna 610 and/or the one or more leads 615. For example, the antenna 610 may include one or more components configured to convert: the received RF signal. The antenna may, for example, receive RF signals having a particular frequency and may ignore any communications (e.g., signals) having a different frequency. At 640, the converted RF signal (e.g., the power source and/or the energy source) may be used to power the antenna 610, the one or more leads 615, or both.

At block 645, the antenna 610 may determine an stimulation operation to be performed on the patient. As described herein, in some examples the determination may be made by the clinician 605 (and communicated by, e.g., a user device). However, in some examples, the RF signal transmitted by the user device of the clinician may include a power signal to power-on the antenna 610, or may include one or more parameters associated with the patient. Thus, upon powering-on, the antenna 610 may determine a stimulation operation to be performed on the patient.

At block 650, the antenna 610 may transmit a second RF signal to the one or more leads 615. As described herein, the antenna 610 may determine (e.g., via receiving a control signal from the clinician 605) a stimulation operation to be performed on a patient. Thus the antenna 610 may generate a RF signal based on the determined operation, and may transmit the RF signal to the one or more leads 615. In some examples, the RF signal may indicate to the one or more leads 615 what operation to be performed on the patient. As described herein, an RF signal may refer to a signal having a rate of oscillation of electromagnetic radio waves in the range of 3 kHz to 300 GHz. Thus, in some examples, a second RF signal may exhibit same or similar characteristics as a RF signal. At block 655, the one or more leads 615 may receive the second control signal.

At block 660, the one or more leads 615 may perform the determined stimulation operation on the patient. As described herein, the one or more leads 615 may be implanted within a patient. For example, the one or more leads 615 may be implanted within a patient's skull (e.g., intracranially), and the stimulation operation may be or may include a deep brain stimulation operation. In some examples, the one or more leads 615 may be implanted within a different portion or organ of a patient's body, and the electrical or electromagnetic therapy operation may be or may include a different operation (e.g., a neuro stimulation operation).

At block 665, upon performing the determined stimulation operation, the one or more leads 615 may transmit feedback from the operation to the antenna 610. In some examples, the one or more leads 615 may transmit the feedback to the clinician 605 via the antenna 610. The feedback may relate to the particular operation performed. For example, if the one or more leads 615 performed a deep brain stimulation operation, the one or more leads 615 may facilitate to monitor one or more parameters associated with the stimulation of the patient's brain, and subsequently transmit the data to the clinician 605 (via the antenna 610). At block 670, the feedback may be received by the clinician 605 (e.g., by a user device of the clinician 605). In some examples, the user device may be configured to display the feedback to the clinician 605 for viewing.

Figure 7:
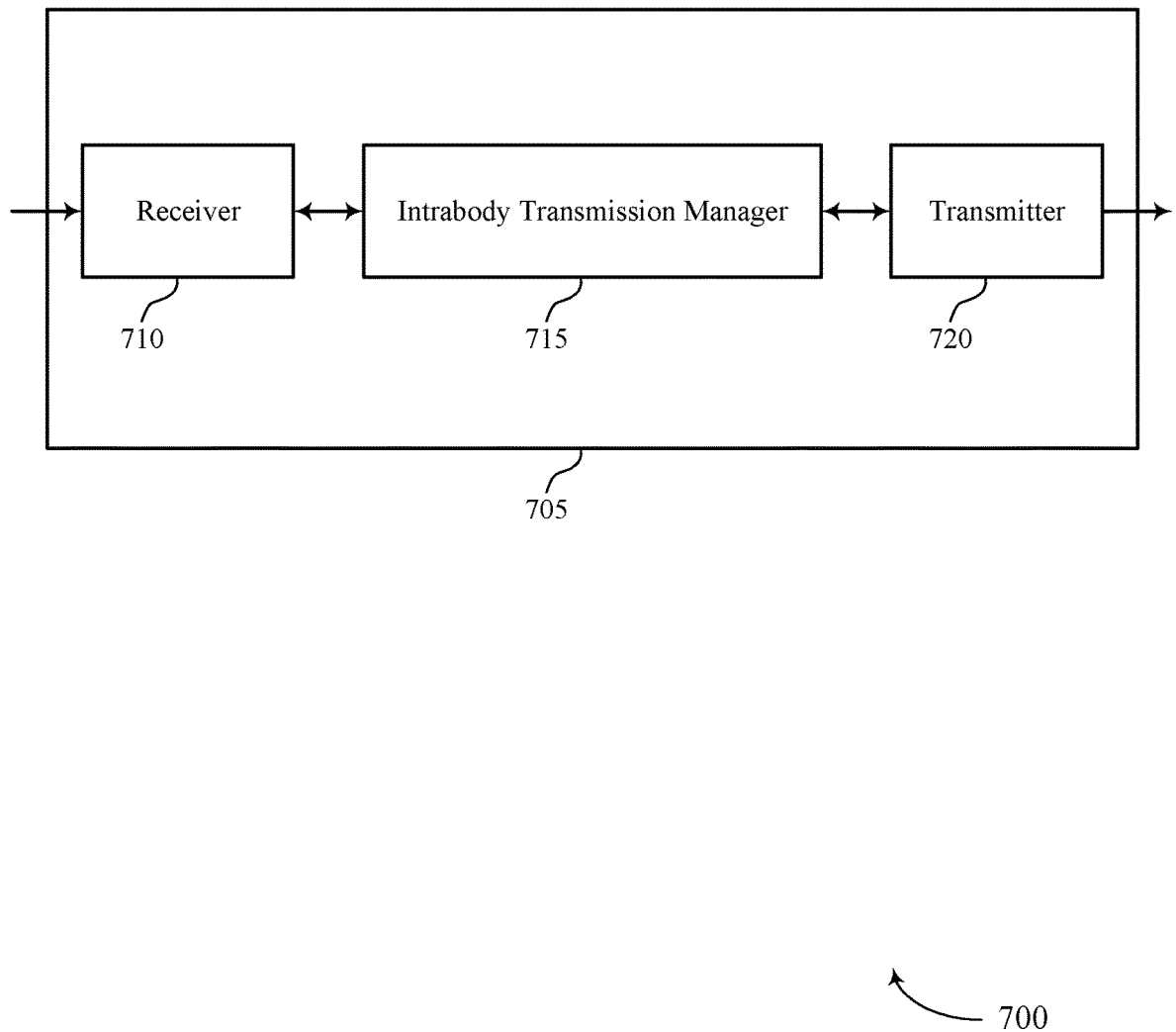
FIGS. 7 and 8 show block diagrams of devices that support passive propagation fractal antenna for intrabody transmissions in accordance with aspects of the present disclosure.

FIG. 7 shows a block diagram 700 of an intrabody transmission server 705 that support passive propagation fractal antenna for intrabody transmissions in accordance with aspects of the present disclosure. The intrabody transmission server 705 may be an example of aspects of a device as described herein. The intrabody transmission server 705 may include a receiver 710, a intrabody transmission manager 715, and a transmitter 720. The intrabody transmission server 705 may also include a processor. Each of these components may be in communication with one another (e.g., via one or more buses).

The receiver 710 may receive information such as packets, user data, or control information associated with various information channels (e.g., control channels, data channels, and information related to extended reality assembly modeling, etc.). Information may be passed on to other components of the intrabody transmission server 705. The receiver 710 may be an example of aspects of the transceiver 1020 described with reference to FIG. 10. The receiver 710 may utilize a single antenna or a set of antennas.

The intrabody transmission manager 715 may support one or more systems, apparatuses, or methods as described herein. The intrabody transmission manager 715 may communicate with one or more apparatuses (e.g., with a fractal antenna) wirelessly or may be located within one or more apparatuses described herein. In some examples, the intrabody transmission manager 715 may receive a control signal from a transmitter in wireless communication with a fractal antenna, determine an electrical or electromagnetic therapy operation to be performed on a patient based at least in part on receiving the control signal, and transmit a second control signal to perform the electrical or electromagnetic therapy operation on the patient. In some examples, the intrabody transmission manager 715 may receive feedback from one or more leads of the fractal antenna. In some examples, the feedback may be associated with the electrical or electromagnetic therapy operation. In some examples, the intrabody transmission manager 715 may transmit the feedback via the fractal antenna.

The intrabody transmission manager 715, or its sub-components, may be implemented in hardware, code (e.g., software or firmware) executed by a processor, or any combination thereof. The intrabody transmission manager 715 may contain encryption system for security of the data transmitted. If implemented in code executed by a processor, the functions of the intrabody transmission manager 715, or its sub-components may be executed by a general-purpose processor, a DSP, an application-specific integrated circuit (ASIC), a FPGA or other programmable logic device, discrete gate or transistor logic, discrete hardware components, or any combination thereof designed to perform the functions described in the present disclosure.

The intrabody transmission manager 715, or its sub-components, may be physically located at various positions, including being distributed such that portions of functions are implemented at different physical locations by one or more physical components. In some examples, the intrabody transmission manager 715, or its sub-components, may be a separate and distinct component in accordance with various aspects of the present disclosure. In some examples, the intrabody transmission manager 715, or its sub-components, may be combined with one or more other hardware components, including but not limited to an input/output (I/O) component, a transceiver, a network server, another computing device, one or more other components described in the present disclosure, or a combination thereof in accordance with various aspects of the present disclosure.

The transmitter 720 may transmit signals generated by other components of the intrabody transmission server 705. In some examples, the transmitter 720 may be collocated with a receiver 710 in a transceiver module. For example, the transmitter 720 may be an example of aspects of the transceiver 1020 described with reference to FIG. 10. The transmitter 720 may utilize a single antenna or a set of antennas (e.g., a set of fractal antennas).

Figure 8:
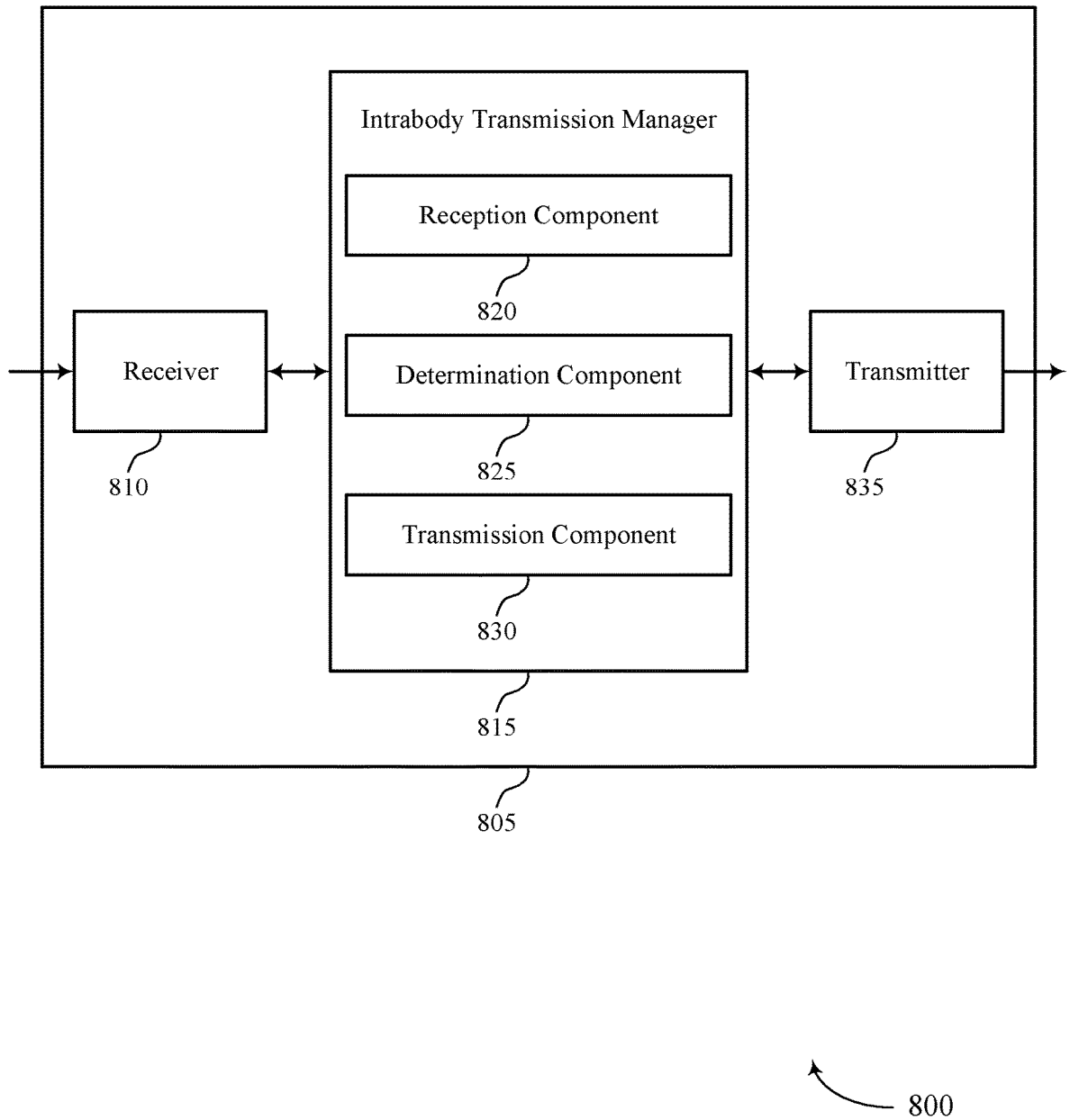

FIG. 8 shows a block diagram 800 of an intrabody transmission component 805 that supports a passive propagation fractal antenna for intrabody transmissions in accordance with aspects of the present disclosure. The intrabody transmission component 805 may be an example of aspects of an intrabody transmission component 805 as described herein. The intrabody transmission component 805 may include a receiver 810, an intrabody transmission manager 815, and a transmitter 835. The intrabody transmission component 805 may also include a processor. Each of these components may be in communication with one another (e.g., via one or more buses).

The receiver 810 may receive information such as packets, user data, or control information associated with various information channels (e.g., control channels, data channels, and information related to extended reality assembly modeling, etc.). Information may be passed on to other components of the intrabody transmission component 805. The receiver 810 may be an example of aspects of the transceiver 1020 described with reference to FIG. 10. The receiver 810 may utilize a single antenna or a set of antennas (e.g., a set of fractal antennas).

The intrabody transmission manager 815 may be an example of aspects of the intrabody transmission manager 815 as described herein. The intrabody transmission manager 815 may include a reception component 820, a determination component 825, and a transmission component 830.

The reception component 820 may receive a control signal from a transmitter in wireless communication with a fractal antenna. In some examples, the reception component 820 may receive feedback from one or more leads. In some examples, the feedback may be associated with the electrical or electromagnetic therapy operation.

The determination component 825 may determine an electrical or electromagnetic therapy operation to be performed on the patient based at least in part on receiving the control signal.

The transmission component 830 may transmit a second control signal to perform the electrical or electromagnetic therapy operation on the patient. In some examples, the transmission component 830 may transmit the feedback via the fractal antenna.

The transmitter 835 may transmit signals generated by other components of the intrabody transmission component 805. In some examples, the transmitter 835 may be collocated with a receiver 810 in a transceiver module. For example, the transmitter 835 may be an example of aspects of the transceiver 1020 described with reference to FIG. 10. The transmitter 835 may utilize a single antenna or a set of antennas (e.g., a set of fractal antennas).

Figure 9:
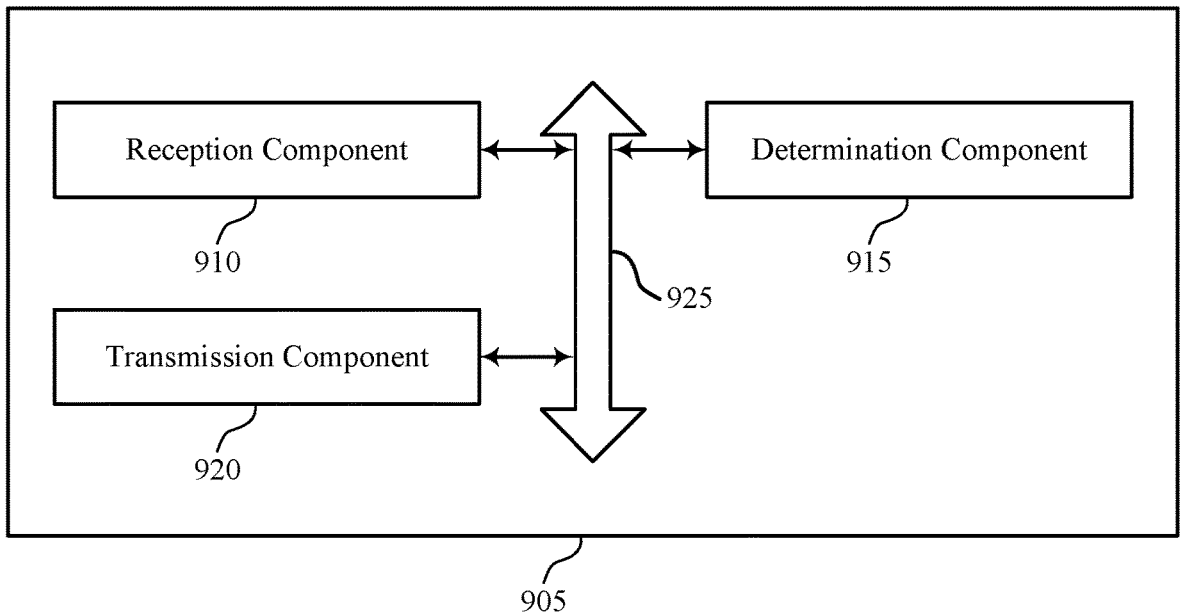
FIG. 9 shows a block diagram of a intrabody transmission component that supports a passive propagation fractal antenna for intrabody transmissions in accordance with aspects of the present disclosure.

FIG. 9 shows a block diagram 900 of an intrabody transmission component 905 that supports a passive propagation fractal antenna for intrabody transmissions in accordance with aspects of the present disclosure. The intrabody transmission component 905 may be an example of aspects of a intrabody transmission manager 715 described with reference to FIG. 7, a intrabody transmission manager 815 described with reference to FIG. 8, or intrabody transmission manager 1010 described with reference to FIG. 10. The intrabody transmission component 905 may include a reception component 910, a determination component 915, and a transmission component 920. Each of these modules may communicate, directly or indirectly, with one another (e.g., via one or more buses 925).

The reception component 910 may receive a control signal from a transmitter in wireless communication with a fractal antenna. In some examples, the reception component 910 may receive feedback from one or more leads. In some examples, the feedback may be associated with the electrical or electromagnetic therapy operation.

The determination component 915 may determine an electrical or electromagnetic therapy operation to be performed on the patient based at least in part on receiving the control signal.

The transmission component 920 may transmit a second control signal to perform the electrical or electromagnetic therapy operation on the patient. In some examples, the transmission component 920 may transmit the feedback via the fractal antenna.

Figure 10:
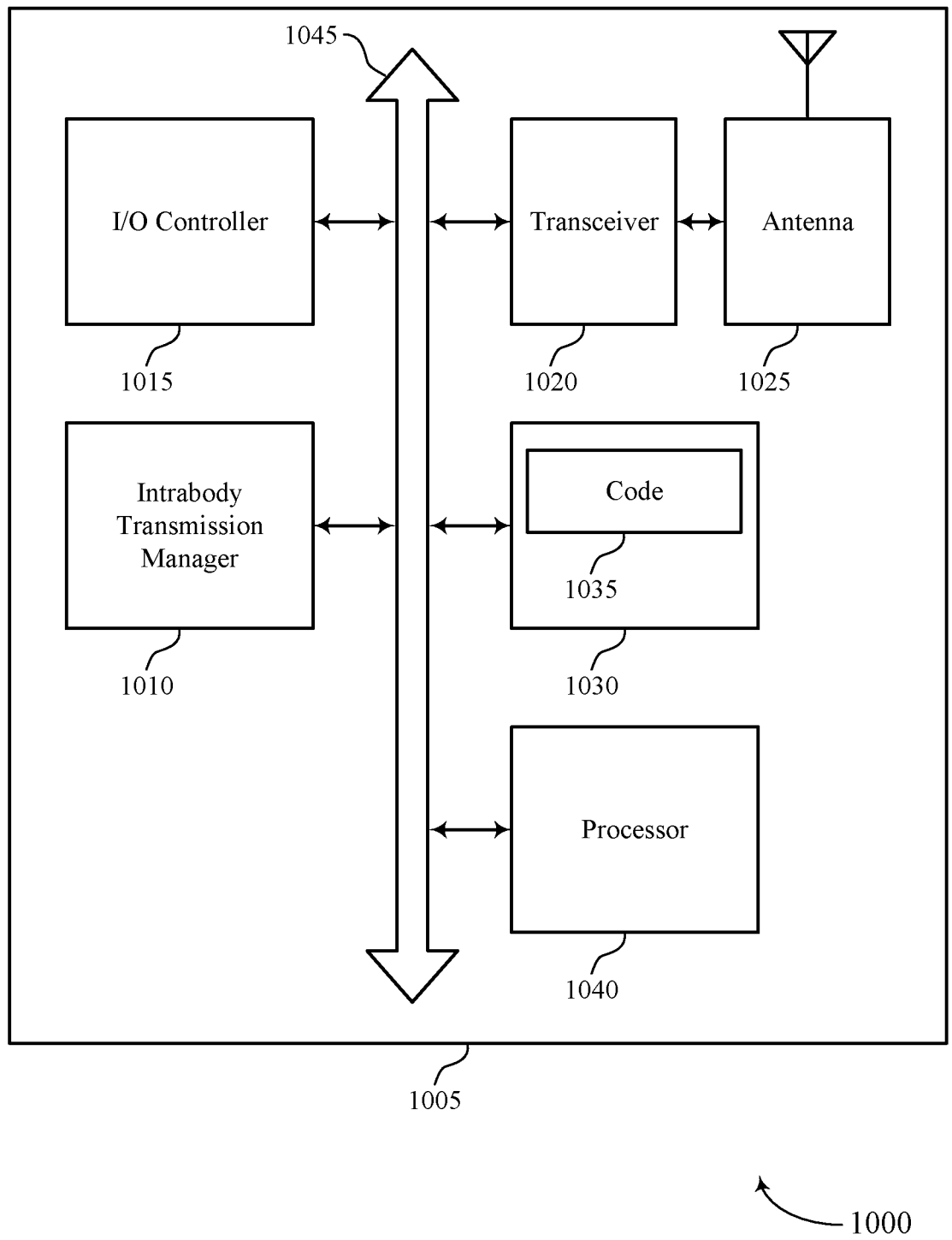
FIG. 10 shows a diagram of a system including a device that supports a passive propagation fractal antenna for intrabody transmissions in accordance with aspects of the present disclosure.

FIG. 10 shows a diagram of a system 1000 including an intrabody transmission server 1005 that supports a passive propagation fractal antenna for intrabody transmissions in accordance with aspects of the present disclosure. The intrabody transmission server 1005 may be an example of or include the components of intrabody transmission server 705 as described with reference to FIG. 7. The intrabody transmission server 1005 may include components for bi-directional voice and data communications including components for transmitting and receiving communications, including a intrabody transmission manager 1010, an I/O controller 1015, a transceiver 1020, an antenna 1025 (e.g., a fractal antenna), memory 1030, and a processor 1040. These components may be in electronic communication via one or more buses (e.g., bus 1045).

The intrabody transmission manager 1010 may receive a control signal from a transmitter in wireless communication with a fractal antenna, determine an electro/electromagnetic therapy operation to be performed on a patient based at least in part on receiving the control signal, and transmit a second control signal to perform the electrical or electromagnetic therapy operation on the patient.

The I/O controller 1015 may manage input and output signals for the intrabody transmission server 1005. The I/O controller 1015 may also manage peripherals not integrated into the intrabody transmission server 1005. In some cases, the I/O controller 1015 may represent a physical connection or port to an external peripheral. In some cases, the I/O controller 1015 may utilize an operating system such as iOS®, ANDROID®, MS-DOS®, MS-WINDOWS®, OS/2®, UNIX®, LINUX®, or another known or advanced operating system. In other cases, the I/O controller 1015 may represent or interact with a modem or router, a keyboard, a mouse, a touchscreen, or a similar device. In some cases, the I/O controller 1015 may be implemented as part of a processor. In some cases, a user may interact with the intrabody transmission server 1005 via the I/O controller 1015 or via hardware components controlled by the I/O controller 1015.

The transceiver 1020 may communicate bi-directionally, via one or more antennas, wired, or wireless links as described above. For example, the transceiver 1020 may represent a wireless transceiver and may communicate bi-directionally with another wireless transceiver. The transceiver 1020 may also include a modem to modulate the packets and provide the modulated packets of data to the antennas for transmission, and to demodulate packets received from the antennas (e.g., the fractal antennas).

In some cases, the wireless device may include a single antenna (e.g., a fractal antenna) 1025. However, in some cases the device may have more than one antenna 1025, which may be capable of concurrently transmitting or receiving multiple wireless transmissions.

The memory 1030 may include RAM and ROM. The memory 1030 may store computer-readable, computer-executable code 1035 including instructions that, when executed, cause the processor to perform various functions described herein. In some cases, the memory 1030 may contain, among other things, a BIOS which may control basic hardware or software operation such as the interaction with peripheral components or devices. The memory 1030 may include encryption features.

The processor 1040 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 1040 may be configured to operate a memory array using a memory controller. In other cases, a memory controller may be integrated into the processor 1040. The processor 1040 may be configured to execute computer-readable instructions stored in a memory (e.g., the memory 1030) to cause the intrabody transmission server 1005 to perform various functions (e.g., functions or tasks supporting extended reality assembly modeling).

The code 1035 may include instructions to implement aspects of the present disclosure, including instructions to support creating a model of a medical device for use in an intrabody transmission system. The code 1035 may be stored in a non-transitory computer-readable medium such as system memory or other type of memory. In some cases, the code 1035 may not be directly executable by the processor 1040 but may cause a computer (e.g., when compiled and executed) to perform functions described herein.

Figure 11:
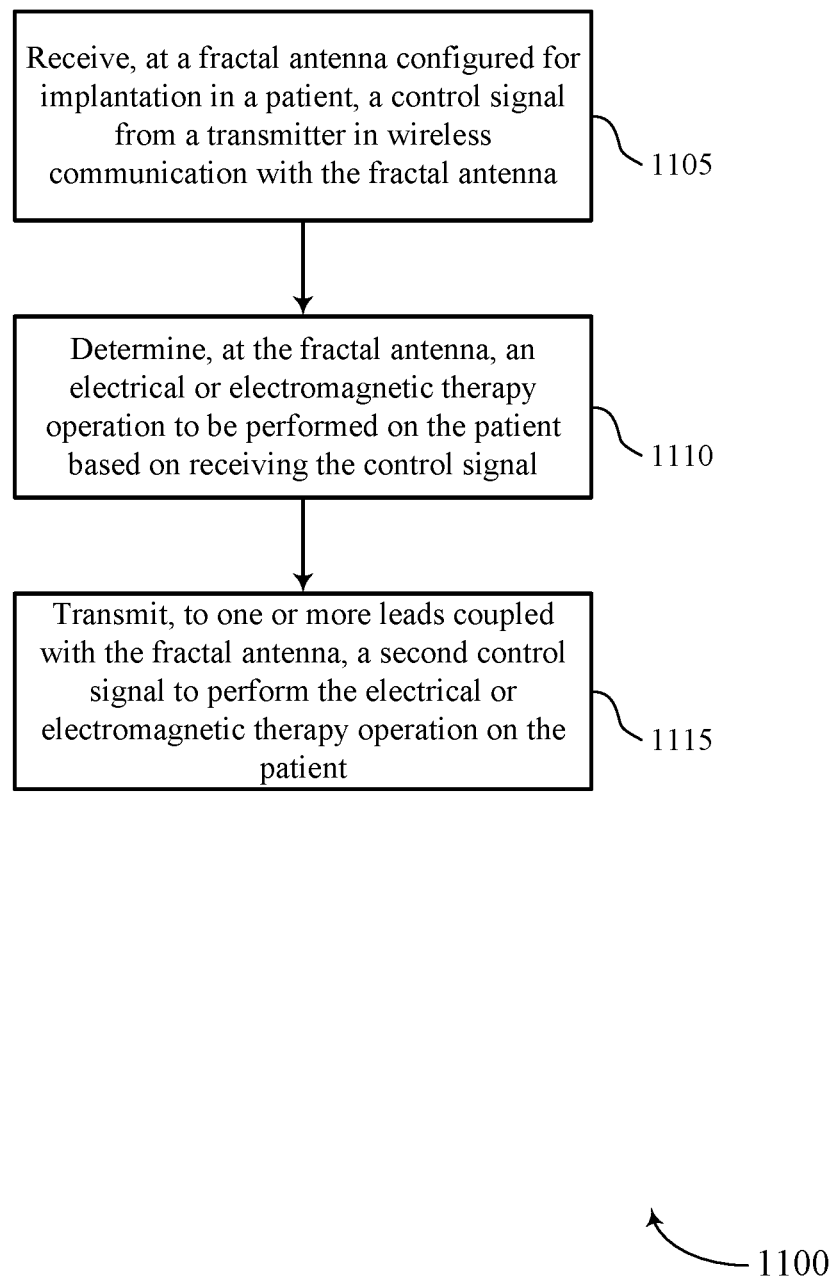
FIGS. 11 and 12 show flowcharts illustrating methods that support passive propagation fractal antenna for intrabody transmissions in accordance with aspects of the present disclosure.

FIG. 11 shows a flowchart illustrating a method 1100 that supports a passive propagation fractal antenna for intrabody transmissions in accordance with aspects of the present disclosure. The operations of method 1100 may be implemented by a intrabody wireless signal transmission system or its components as described herein. For example, the operations of method 1100 may be performed by a intrabody transmission component 905 as described with reference to FIG. 9. In some examples, a intrabody wireless signal transmission system may execute a set of instructions to control the functional elements of the intrabody wireless signal transmission system to perform the functions described below. Additionally or alternatively, a intrabody wireless signal transmission system may perform aspects of the functions described below using special-purpose hardware.

At 1105, the intrabody wireless signal transmission system may receive, at a fractal antenna configured to be affixed cranially on a patient, a control signal from a transmitter in wireless communication with the fractal antenna. The operations of 1105 may be performed according to the methods described herein. In some examples, aspects of the operations of 1105 may be performed by a reception component 910 as described with reference to FIG. 9.

At 1110, the intrabody wireless signal transmission system may determine, at the fractal antenna, an electrical or electromagnetic therapy operation to be performed on the patient based on receiving the control signal. The operations of 1110 may be performed according to the methods described herein. In some examples, aspects of the operations of 1110 may be performed by a determination component 915 as described with reference to FIG. 9.

At 1115, the intrabody wireless signal transmission system may transmit, to one or more leads coupled with the fractal antenna, a second control signal to perform the electrical or electromagnetic therapy operation on the patient. The operations of 1115 may be performed according to the methods described herein. In some examples, aspects of the operations of 1115 may be performed by a transmission component 920 as described with reference to FIG. 9.

Figure 12:
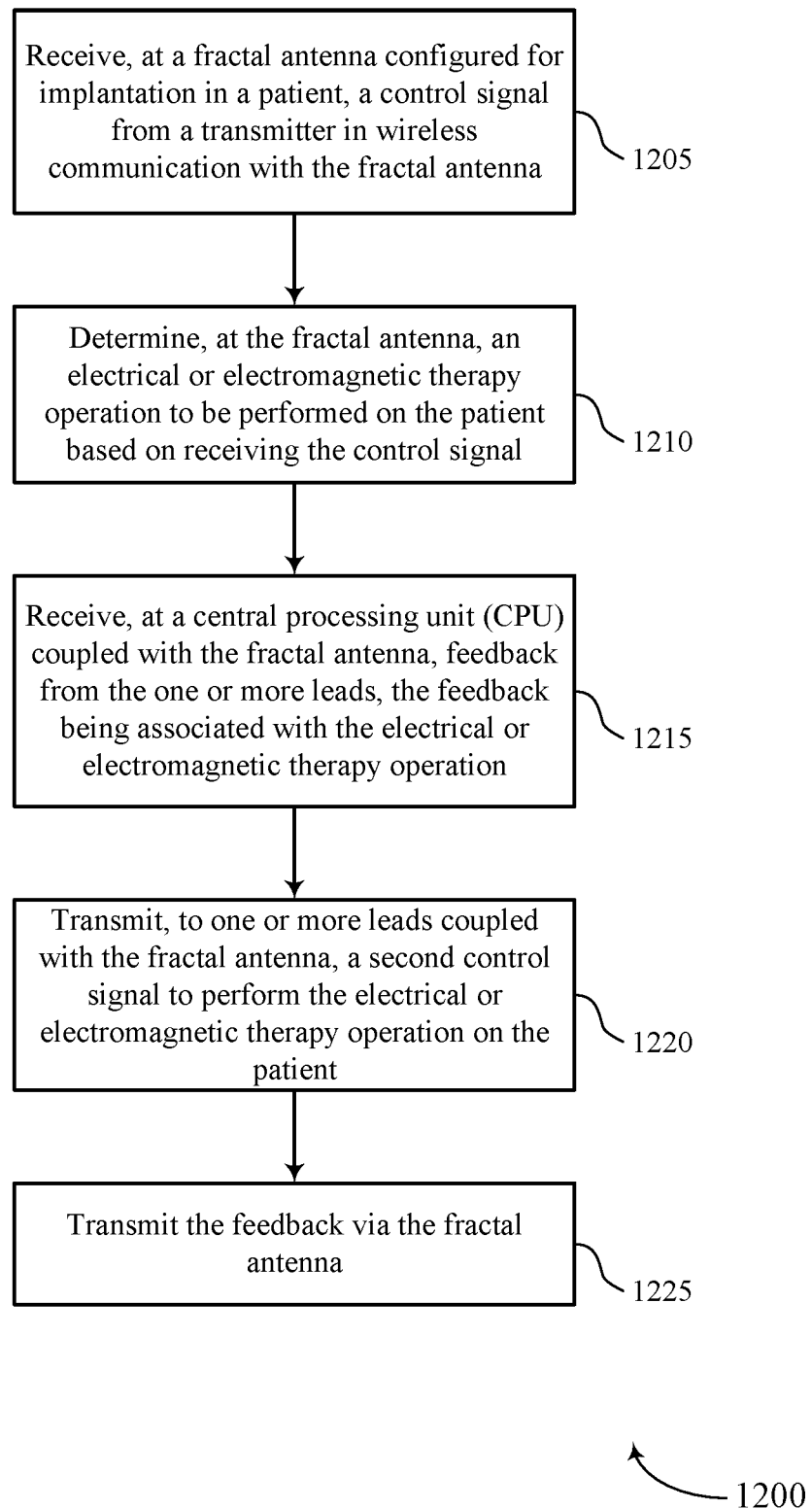

FIG. 12 shows a flowchart illustrating a method 1200 that supports a passive propagation fractal antenna for intrabody transmissions in accordance with aspects of the present disclosure. The operations of method 1200 may be implemented by a intrabody wireless signal transmission system or its components as described herein. For example, the operations of method 1200 may be performed by a intrabody transmission component 905 as described with reference to FIG. 9. In some examples, a intrabody wireless signal transmission system may execute a set of instructions to control the functional elements of the intrabody wireless signal transmission system to perform the functions described below. Additionally or alternatively, a intrabody wireless signal transmission system may perform aspects of the functions described below using special-purpose hardware.

At 1205, the intrabody wireless signal transmission system may receive, at a fractal antenna configured to be affixed cranially on a patient, a control signal from a transmitter in wireless communication with the fractal antenna. The operations of 1205 may be performed according to the methods described herein. In some examples, aspects of the operations of 1205 may be performed by a reception component 910 as described with reference to FIG. 9.

At 1210, the intrabody wireless signal transmission system may determine, at the fractal antenna, an electrical or electromagnetic therapy operation to be performed on the patient based on receiving the control signal. The operations of 1210 may be performed according to the methods described herein. In some examples, aspects of the operations of 1210 may be performed by a determination component 915 as described with reference to FIGs. FIG. 9.

At 1215, the intrabody wireless signal transmission system may receive, at a central processing unit (CPU) coupled with the fractal antenna, feedback from the one or more leads, the feedback being associated with the electrical or electromagnetic therapy operation. The operations of 1215 may be performed according to the methods described herein. In some examples, aspects of the operations of 1215 may be performed by a reception component 910 as described with reference to FIG. 9.

At 1220, the intrabody wireless signal transmission system may transmit, to one or more leads coupled with the fractal antenna, a second control signal to perform the electrical or electromagnetic therapy operation on the patient. The operations of 1220 may be performed according to the methods described herein. In some examples, aspects of the operations of 1220 may be performed by a transmission component as described with reference to FIG. 9.

At 1225, the intrabody wireless signal transmission system may transmit the feedback via the fractal antenna. The operations of 1225 may be performed according to the methods described herein. In some examples, aspects of the operations of 1225 may be performed by a transmission component 920 as described with reference to FIG. 9.

It should be noted that the methods described above describe possible implementations, and that the operations and the steps may be rearranged or otherwise modified, and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, infrared fields, or any combination thereof.

The various illustrative blocks and modules described in connection with the disclosure herein may be implemented or performed with a general-purpose processor, a digital signal processor (DSP), an ASIC, an field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration). A processor may in some cases be in electronic communication with a memory, where the memory stores instructions that are executable by the processor. Thus, the functions described herein may be performed by one or more other processing units (or cores), on at least one integrated circuit (IC). In various examples, different types of ICs may be used (e.g., Structured/Platform ASICs, an FPGA, or another semi-custom IC), which may be programmed in any manner known in the art. The functions of each unit may also be implemented, in whole or in part, with instructions embodied in a memory, formatted to be executed by one or more general or application-specific processors.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above may be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media may comprise RAM, ROM, electrically erasable programmable read only memory (EEPROM), compact disk (CD) ROM or other optical disk storage, magnetic disk storage or other magnetic storage devices, or any other non-transitory medium that may be used to carry or store desired program code means in the form of instructions or data structures and that may be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, digital subscriber line (DSL), or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A system for wireless signal transmission, comprising:
  a fractal antenna configured to be affixed cranially on a patient, wherein the fractal antenna comprises a first portion and a second portion each having one or more antenna elements of a first geometry and one or more antenna elements of a second geometry that is different than the first geometry, wherein an antenna element pattern of the first portion is symmetric with an antenna element pattern of the second portion with respect to a first central axis of the fractal antenna, and wherein an antenna element pattern of a first subset of the first portion is symmetric with an antenna element pattern of a second subset of the first portion with respect to a second central axis of the fractal antenna that is perpendicular to the first central axis of the fractal antenna;
  one or more leads coupled with the fractal antenna and configured for implantation in the patient, wherein the one or more leads are configured to deliver an electrical or electromagnetic signal to the patient; and
  a transmitter in wireless communication with the fractal antenna, wherein the transmitter is configured to wirelessly transmit a control signal relating to the electrical or electromagnetic signal to the fractal antenna, wherein the one or more leads are configured to deliver the electrical or electromagnetic signal to the patient based at least in part on the fractal antenna receiving the control signal.

2. The system of claim 1, further comprising:
  a central processing unit (CPU) coupled with the fractal antenna, wherein the CPU is configured to process the received control signal.

3. The system of claim 2, wherein the one or more leads are further configured to receive biometric data associated with the patient.

4. The system of claim 3, wherein the CPU is configured to process the biometric data associated with the patient for transmission via the fractal antenna.

5. The system of claim 2, wherein the CPU is configured to authenticate the transmitter and the fractal antenna based at least in part on receiving the control signal.

6. The system of claim 2, wherein the CPU comprises a radio frequency (RF) chip, and wherein the control signal comprises a RF signal.

7. The system of claim 6, wherein the RF chip is configured to convert the RF signal into a power source or an energy source for the fractal antenna, the one or more leads, or both.

8. The system of claim 1, wherein the electrical or electromagnetic signal is configured for deep brain stimulation.

9. The system of claim 1, wherein the fractal antenna comprises circuitry that is configured to power on based at least in part on receiving the control signal from the transmitter.

10. The system of claim 1, wherein the transmitter is configured for subcutaneous implantation.

11. The system of claim 1, wherein the fractal antenna comprises a flexible structure.

12. An apparatus for wireless signal transmission, comprising:
  a fractal antenna configured to be affixed cranially on a patient, wherein the fractal antenna comprises a first portion and a second portion each having one or more antenna elements of a first geometry and one or more antenna elements of a second geometry that is different than the first geometry, wherein an antenna element pattern of the first portion is symmetric with an antenna element pattern of the second portion with respect to a first central axis of the fractal antenna, and wherein an antenna element pattern of a first subset of the first portion first subset is symmetric with an antenna element pattern of a second subset of the first portion with respect to a second central axis of the fractal antenna that is perpendicular to the first central axis of the fractal antenna; and
  one or more leads coupled with the fractal antenna and configured for implantation in the patient, wherein the one or more leads are configured to deliver an electrical or electromagnetic signal to the patient based at least in part on control signals received by the fractal antenna.

13. The apparatus of claim 12, wherein the one or more leads are further configured to receive biometric data associated with the patient and communicate the biometric data to the fractal antenna.

14. The apparatus of claim 12, wherein the fractal antenna is configured to wirelessly transmit feedback associated with the electrical or electromagnetic signal.

15. The apparatus of claim 12, wherein the one or more leads are configured for intercranial implantation in the patient.

16. The apparatus of claim 12, wherein the fractal antenna and the one or more leads each comprise a bio-inert coating.

17. The apparatus of claim 12, wherein the fractal antenna is configured to receive a multi-band or wide-band radio frequency (RF) signal.

18. The apparatus of claim 12, wherein the fractal antenna comprises at least one self-similar design.

* * * * *